US009913841B2

(12) United States Patent
Van der Graaf et al.

(10) Patent No.: US 9,913,841 B2
(45) Date of Patent: Mar. 13, 2018

(54) 6-HYDROXY-2,5,7,8-TETRAMETHYLCHROMAN-COMPOUNDS FOR THE TREATMENT OF CHRONIC OBSTRUCTIVE AIRWAY DISEASES

(71) Applicant: Sulfateq B.V., Groningen (NL)

(72) Inventors: Adrianus Cornelis Van der Graaf, Groningen (NL); Martina Schmidt, Haren (NL); Gerrit Jan Willem Euverink, Haren (NL); Hermanus Meurs, Groningen (NL); Robert Henk Henning, Groningen (NL)

(73) Assignee: Sulfateq B.V., Groningen (NL)

( * ) Notice: Subject to any disclaimer, the term of this patent is extended or adjusted under 35 U.S.C. 154(b) by 0 days.

(21) Appl. No.: 15/318,635

(22) PCT Filed: Jun. 17, 2015

(86) PCT No.: PCT/EP2015/063579
§ 371 (c)(1),
(2) Date: Dec. 13, 2016

(87) PCT Pub. No.: WO2015/193365
PCT Pub. Date: Dec. 23, 2015

(65) Prior Publication Data

US 2017/0151234 A1 Jun. 1, 2017

(30) Foreign Application Priority Data

Jun. 17, 2014 (NL) .................................... 2013012

(51) Int. Cl.
*A61K 31/496* (2006.01)
*A61K 31/353* (2006.01)
*A61K 31/4025* (2006.01)
*A61K 9/00* (2006.01)

(52) U.S. Cl.
CPC .......... *A61K 31/496* (2013.01); *A61K 9/0075* (2013.01); *A61K 31/353* (2013.01); *A61K 31/4025* (2013.01)

(58) Field of Classification Search
CPC .. A61K 31/496; A61K 9/0075; A61K 31/353; A61K 31/4025
USPC .......................................... 544/376; 549/405
See application file for complete search history.

(56) References Cited

U.S. PATENT DOCUMENTS

| | | | |
|---|---|---|---|
| 5,290,797 | A | 3/1994 | Le Baut et al. |
| 5,315,017 | A | 5/1994 | Le Baut et al. |
| 2004/0122059 | A1 | 6/2004 | Cantoma et al. |
| 2005/0065009 | A1 | 3/2005 | Lu et al. |

FOREIGN PATENT DOCUMENTS

| | | | |
|---|---|---|---|
| EP | 0202580 | A2 | 11/1986 |
| JP | S59222415 | A | 12/1984 |
| WO | WO8808424 | A1 | 11/1988 |
| WO | WO2004045556 | A2 | 6/2004 |
| WO | WO2014098586 | A1 | 6/2014 |

OTHER PUBLICATIONS

Han et al., The Anti-Inflammatory and Bronchodilating Properties of the Novel Pharmacological Compound Sul-121, (Epi) genetics in Pharmacology Nederlandse Vereninging voor Farmacologie Radboud UMC Nijmegen, Apr. 24, 2015, XP002742182, Retrieved from the Internet: URL:http://www.uvfarmaco.nl/assets/docs/Ab [retrieved on Jul. 14, 2015] abstract, 2 pages.

*Primary Examiner* — Kahsay Habte

(57) ABSTRACT

The present invention relates to compounds for the treatment of chronic obstructive airway diseases such as chronic obstructive pulmonary disease (COPD) or asthma or bronchiectasis. The present invention further relates to drug delivery devices suitable to be used in the treatment of chronic obstructive airway diseases such as a nebulizer comprising the present compounds. Specifically, the present invention relates to (6-hydroxy-2,5,7,8-tetramethylchroman-2-yl)(piperazin-1-yl)methanone or N,6-di-hydroxy-2,5,7,8-tetramethylchroman-2-carboxamide or a pharmaceutically acceptable salt or base thereof for use in the treatment of chronic obstructive airway diseases, preferably chronic obstructive pulmonary disease (COPD) or asthma or bronchiectasis, more preferably chronic obstructive pulmonary disease (COPD).

8 Claims, 8 Drawing Sheets

*: p<0.05, two-way ANOVA.
#: p<0.05, One-way repeated measures ANOVA.

6-HYDROXY-2,5,7,8-TETRAMETHYLCHROMAN-COMPOUNDS FOR THE TREATMENT OF CHRONIC OBSTRUCTIVE AIRWAY DISEASES

The present invention relates to compounds for the treatment of chronic obstructive airway diseases such as chronic obstructive pulmonary disease (COPD) or asthma or bronchiectasis. The present invention further relates to drug delivery devices suitable to be used in the treatment of chronic obstructive airway diseases such as a nebulizer comprising the present compounds.

Chronic obstructive pulmonary disease (COPD), also designated as chronic obstructive lung disease (COLD) or chronic obstructive airway disease (COAD) is a type of obstructive lung disease characterized by chronic obstruction of the airflow in the lungs. The main symptoms of chronic obstructive pulmonary disease (COPD) include shortness of breath, cough, and sputum production.

Tobacco smoking is the most common cause of chronic obstructive pulmonary disease (COPD) but also other causative factor s are known such as air pollution and genetics.

Chronic obstructive pulmonary disease (COPD) can be prevented by reducing exposure to the known causes. This includes efforts to decrease rates of smoking and to improve indoor and outdoor air quality. Chronic obstructive pulmonary disease (COPD) treatments include: quitting smoking, vaccinations, rehabilitation, and often inhaled bronchodilators and steroids. Some people may benefit from long-term oxygen therapy or lung transplantation.

Worldwide, chronic obstructive pulmonary disease (COPD) affects 329 million people or nearly 5% of the population. In 2011, it ranked as the fourth-leading cause of death, killing over 3 million people. The number of deaths is projected to increase due to higher smoking rates and an aging population in many countries.

Asthma is a common chronic inflammatory disease of the airways characterized by variable and recurring symptoms, reversible airflow obstruction and bronchospasm. Common symptoms include wheezing, coughing, chest tightness, and shortness of breath.

Asthma is thought to be caused by a combination of genetic and environmental factors. Its diagnosis is usually based on the pattern of symptoms, response to therapy over time and spirometry. Asthma is clinically classified according to the frequency of symptoms, forced expiratory volume in one second (FEV1), and peak expiratory flow rate. Asthma may also be classified as atopic (extrinsic) or non-atopic (intrinsic) where atopy refers to a predisposition toward developing type 1 hypersensitivity reactions.

Treatment of acute symptoms is usually with an inhaled short-acting beta-2 agonist (such as salbutamol) and oral corticosteroids. In very severe cases, intravenous corticosteroids, magnesium sulfate, and hospitalization may be required. Symptoms can be prevented by avoiding triggers, such as allergens and irritants, and by the use of inhaled corticosteroids. Long-acting beta agonists (LABA) or leukotriene antagonists may be used in addition to inhaled corticosteroids if asthma symptoms remain uncontrolled.

The occurrence of asthma has increased significantly since the 1970s. In 2011, 235-300 million people globally have been diagnosed with asthma and the number of deaths wherein asthma is the causative factor is estimated to be 250,000 deaths annually.

Bronchiectasis is a disease characterized by localized, irreversible dilation of part of the bronchial tree caused by the break down of the muscle and elastic tissue. It is classified as an obstructive lung disease, along with emphysema, bronchitis, and asthma.

Involved bronchi are dilated, inflamed, and easily collapsible, resulting in airway obstruction and impaired clearance of secretions. Bronchiectasis may result from a variety of infective and acquired causes, including severe and recurrent pneumonia, tuberculosis, and cystic fibrosis. Bronchiectasis has both congenital and acquired causes, with the latter more frequent.

Tuberculosis, pneumonia, inhaled foreign bodies, allergic bronchopulmonary aspergillosis and bronchial tumours are the major acquired causes of Bronchiectasis. Infective acquired causes associated with Bronchiectasis include infections caused by the *Staphylococcus, Klebsiella* or *Bordetella pertussis*. Further, aspiration of ammonia and other toxic gases, pulmonary aspiration, alcoholism, heroin (drug use) and various allergies appear to be linked to the development of Bronchiectasis.

Bronchiectasis may also result from congenital causes that affect cilia motility or ion transport. Kartagener syndrome is one such disorder of cilia motility linked to the development of bronchiectasis. Another common cause is cystic fibrosis affecting chloride ion transport. Young's syndrome, which is clinically similar to cystic fibrosis, is thought to significantly contribute to the development of bronchiectasis. This is due to the occurrence of chronic infections of the sinuses and bronchiole tree. Other less-common congenital causes include primary immunodeficiencies, due to the weakened or nonexistent immune system response to severe, recurrent infections that commonly affect the lung.

Chronic obstructive airway diseases, such as asthma, chronic obstructive pulmonary disease (COPD) and bronchiectasis, are characterized by a chronic inflammation and bronchoconstriction, causing airways obstruction and difficulties to breath. Current therapy includes treatment with bronchodilators, including β2-adrenergic receptor (β2-AR) agonists and anti-inflammatory agents like corticosteroids. β2-agonists are not effective as anti-inflammatory drugs in vivo. Ideally, a drug has both bronchodilating and anti-inflammatory actions, without a risk of desensitization. Irrespective of a specific mode of action, preferably, a drug lowers the constriction and, or lowers the inflammation, which has a positive effect on the efficacy of the lungs.

It is an object of the present invention, amongst other objects, to provide compounds for the treatment of chronic obstructive airway diseases, such as asthma, chronic obstructive pulmonary disease (COPD) and bronchiectasis and especially chronic obstructive pulmonary disease (COPD) or asthma. In providing such compounds, the compound preferably meet one or more of the modes of action for a medicament for the treatment of chronic obstructive airway diseases, i.e. compounds having bronchodilating and anti-inflammatory effects. Preferably, the compounds remain active over long term administration, i.e., the compounds show little desensitization.

The above object, amongst other objects, is met by the present invention by as outlined in the appended claims.

The above object is met by a compound according to formula (I), or a pharmaceutically acceptable salt or base thereof, for use in the treatment of chronic obstructive airway diseases,

I

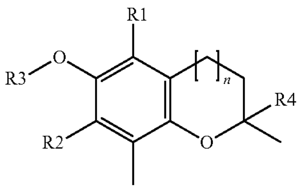

wherein R1 and R2 may be the same or different, and represent a C1-C4 linear or branched alkylgroup;

wherein R3 represents a hydrogen or prodrug moiety that can be removed in living tissue; preferably, R3 forms together with the 6-oxygen an ester group. R3 may have 1-12 carbon atoms, preferably 1-6 carbon atoms, and may comprise one or more amine or oxygen atoms;

n may be 0 or 1, and is preferably 1;

R4 is a group comprising at 1-20 carbon atoms and at least one nitrogen atom; R4 may comprise further nitrogen atoms, one or more oxygen atoms, halogen, sulphur or phosphor atoms and R4 may comprise aromatic groups, wherein the molecular weight of R4 preferably is less than 300 Da;

wherein the compound is in a formulation suitable for inhalation.

As will be recognized, the compound of formula (I) is derived from trolox, a water soluble analogue of vitamin E. In trolox, R1 and R2 are methyl, R3 is hydrogen, and R4 is carboxylic acid.

Specifically, the above object, amongst other objects, is met by the present invention by a compound according to the formula (II)

(II)

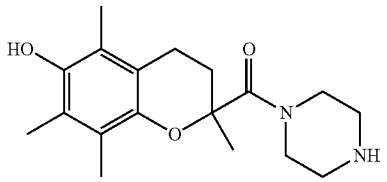

(6-hydroxy-2,5,7,8-tetramethylchroman-2-yl)(piperazin-1-yl)methanone or a pharmaceutically acceptable salt or base thereof for use in the treatment of chronic obstructive airway diseases, preferably chronic obstructive pulmonary disease (COPD) or asthma or bronchiectasis, more preferably chronic obstructive pulmonary disease (COPD).

According to the present invention, according to a further aspect, the above object, amongst other objects, are met by a compound according to the formula (III)

(III)

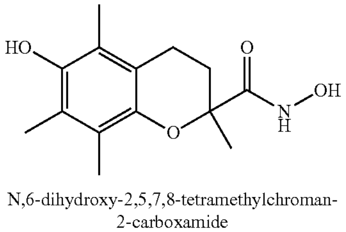

N,6-dihydroxy-2,5,7,8-tetramethylchroman-2-carboxamide or a pharmaceutically acceptable salt or base thereof for use in the treatment of chronic obstructive airway diseases, preferably chronic obstructive pulmonary disease (COPD) or asthma or bronchiectasis, more preferably chronic obstructive pulmonary disease (COPD).

According to the present invention, according to a further aspect, the above object, amongst other objects, are met by a compound selected from the group, together "group A", consisting of 2,2,5,7,8-pentamethylchroman-6-ol; (S)-6-hydroxy-2,5,7,8-tetramethylchroman-2-carboxylic acid; (R)-6-hydroxy-2,5,7,8-tetramethylchroman-2-carboxylic acid; 6-hydroxy-2,5,7,8-tetramethylchroman-2-carboxamide; N-butyl-6-hydroxy-2,5,7,8-tetramethylchroman-2-carboxamide; 6-hydroxy-N-isopropyl-2,5,7,8-tetramethylchroman-2-carboxamide; (E)-N-(3,7-dimethylocta-2,6-dien-1-yl)-6-hydroxy-2,5,7,8-tetramethylchroman-2-carboxamide; (6-hydroxy-2,5,7,8-tetramethylchroman-2-yl)(morpholino) methanone; N-(4-fluorobenzyl)-6-hydroxy-2,5,7,8-tetramethylchroman-2-carboxamide; 6-hydroxy-N—((S)-2-hydroxy-1-phenylethyl)-2,5,7,8-tetramethylchroman-2-carboxamide; 6-hydroxy-2,5,7,8-tetramethyl-N-(2-(methylamino)ethyl)chroman-2-carboxamide; 6-hydroxy-N,2,5,7,8-pentamethyl-N-(2-(methylamino)ethyl)chroman-2-carboxamide; 6-hydroxy-2,5,7,8-tetramethyl-N-(3-(piperidin-1-yl)propyl)chroman-2-carboxamide; 6-hydroxy-2,5,7,8-tetramethyl-N-(3-nitrophenyl)chroman-2-carboxamide; N-(4-fluorophenyl)-6-hydroxy-2,5,7,8-tetramethylchroman-2-carboxamide; methyl 4-(6-hydroxy-2,5,7,8-tetramethylchroman-2-carboxamido)benzoate; (4-butylpiperazin-1-yl)(6-hydroxy-2,5,7,8-tetramethylchroman-2-yl)methanone; (6-hydroxy-2,5,7,8-tetramethylchroman-2-yl)(4-(2-hydroxyethyl)piperazin-1-yl)methanone; ((2S,5R)-4-allyl-2,5-dimethylpiperazin-1-yl)(6-hydroxy-2,5,7,8-tetramethylchroman-2-yl)methanone; N—((R)-2-amino-2-oxo-1-phenylethyl)-6-hydroxy-2,5,7,8-tetramethylchroman-2-carboxamide; (6-hydroxy-2,5,7,8-tetramethylchroman-2-yl)((S)-2-(hydroxymethyl) pyrrolidin-1-yl)methanone; N-(2-bromoethyl)-6-hydroxy-2,5,7,8-tetramethylchroman-2-carboxamide; N'-(2-cyanoethyl)-6-hydroxy-2,5,7,8-tetramethylchroman-2-carbohydrazide; 2-(((4-fluorobenzyl)amino)methyl)-2,5,7,8-tetramethylchroman-6-ol; 2-((butylamino)methyl)-2,5,7,8-tetramethylchroman-6-ol; 6-hydroxy-5,7-diisopropyl-2,8-dimethylchroman-2-carboxylic acid; 2-(hydroxymethyl)-5,7-diisopropyl-2,8-dimethylchroman-6-ol; 6-hydroxy-N—((R)-1-hydroxypropan-2-yl)-2,5,7,8-tetramethylchroman-2-carboxamide; (6-hydroxy-2,5,7,8-tetramethylchroman-2-yl) (4-(2-(2-hydroxyethoxy)ethyl)piperazin-1-yl)methanone; N-(2-cyanoethyl)-6-hydroxy-2,5,7,8-tetramethylchroman-2-carboxamide; 6-hydroxy-N-(2-((2-hydroxyethyl)(methyl) amino)ethyl)-2,5,7,8-tetramethylchroman-2-carboxamide; (R)—N,6-dihydroxy-2,5,7,8-tetramethylchroman-2-carboxamide; (S)—N,6-dihydroxy-2,5,7,8-tetramethylchroman-2-carboxamide; 2-(((S)-2-(hydroxymethyl)pyrrolidin-1-yl) methyl)-2,5,7,8-tetramethylchroman-6-ol; 2-((((S)-2-hydroxy-1-phenylethyl)amino)methyl)-2,5,7,8-tetramethylchroman-6-ol; 2,5,7,8-tetramethyl-2-(piperidin-1-ylmethyl)chroman-6-ol; N,6-dihydroxy-5,7-diisopropyl-2,8-dimethylchroman-2-carboxamide; (6-hydroxy-2,5,7,8-tetramethylchroman-2-yl)(4-(2-hydroxyethyl)piperazin-1-yl)methanone; (6-hydroxy-5,7-diisopropyl-2,8-dimethylchroman-2-yl)(4-(2-hydroxyethyl)piperazin-1-yl) methanone; 2-(((S)-2-(hydroxymethyl)pyrrolidin-1-yl) methyl)-2,5,7,8-tetramethylchroman-6-ol; 2-(((S)-2-(hydroxymethyl)pyrrolidin-1-yl)methyl)-2,5,7,8-tetramethylchroman-6-ol; 2-(4-(6-hydroxy-2,5,7,8- tetramethylchroman-2-carbonyl)piperazin-1-yl)acetic acid; (6-hydroxy-5,7-diisopropyl-2,8-dimethylchroman-2-yl) (piperazin-1-yl)methanone; (6-hydroxy-2,5,7,8-tetramethylchroman-2-yl)(4-(2-hydroxyethyl)piperazin-1-yl)methanone; 2-(4-(6-hydroxy-5,7-diisopropyl-2,8-dimethylchroman-2-carbonyl)piperazin-1-yl)acetic acid; ethyl 2-(4-(6-hydroxy-2,5,7,8-tetramethylchroman-2-carbonyl)piperazin-1-yl)acetate; (S)-2-(4-(6-hydroxy-2,5,7,8-tetramethylchroman-2-carbonyl)piperazin-1-yl)acetic acid; (R)-2-(4-(6-hydroxy-2,5,7,8-tetramethylchroman-2-carbonyl)piperazin-1-yl)acetic acid; (2S)-1-(6-hydroxy-2,5,7,8-tetramethylchroman-2-carbonyl)pyrrolidine-2-carboxylic acid; (2S)-1-(6-hydroxy-2,5,7,8-tetramethylchroman-2-carbonyl)pyrrolidine-2-carboxylic acid; (2S)-1-(6-hydroxy-2,5,7,8-tetramethylchroman-2-carbonyl)pyrrolidine-2-carboxylic acid and pharmaceutically acceptable salts or bases thereof for use in the treatment of chronic obstructive airway diseases, preferably chronic obstructive pulmonary disease (COPD) or asthma or bronchiectasis, more preferably chronic obstructive pulmonary disease (COPD).

The present inventors surprisingly discovered that the present compounds according to formula (I), and most preferably (6-hydroxy-2,5,7,8-tetramethylchroman-2-yl) (piperazin-1-yl)methanone or N,6-dihydroxy-2,5,7,8-tetramethylchroman-2-carboxamide have an apparent bronchodilating and anti-inflammatory effect making them suitable for the treatment of obstructive airways diseases and, especially, making them suitable for the treatment of chronic obstructive pulmonary disease (COPD) and asthma.

According to a preferred embodiment of the present invention, the present treatment of chronic obstructive airway diseases comprises administration of the present compounds such as the compounds according formula (I), (II), and (III), or according to group A, through inhalation. Inhalation as used herein indicates a route of administration where the present compounds are taken in through the mouth or nose, to arrive into the lungs.

The compound according to formula (I),

I

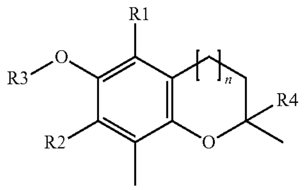

preferably has the following characteristics:

R1 and R2 may be the same or different, and represent a C1-C4 linear or branched alkylgroup. Preferably, R1 and R2 are methyl, ethyl or isopropyl, and most preferably, R1 and R3 are the same, and are methyl or isopropyl. Other suitable groups are n-butyl and t-butyl.

R3 represents a hydrogen or prodrug moiety that can be removed in living tissue. Preferably, R3 forms together with the 6-oxygen an ester group. R3 may have 1-12 carbon atoms, preferably 1-6 carbon atoms, and may comprise one or more amine or oxygen atoms. Suitable groups—together with the 6-oxygen—include ethyl-ester, butyl-ester, benzoyl-ester, or an ester of an amino-acid, or amino acids wherein the aminogroup is amidated with an alkyl carboxylic acid having 1-4 carbon atoms. In one preferred embodiment, R3 is hydrogen.

n may be 0 or 1, and is preferably 1;

R4 is a group comprising at 1-20 carbon atoms and at least one nitrogen atom. R4 may comprise further nitrogen atoms, one or more oxygen atoms, halogen, sulphur or phosphor atoms and R4 may comprise aromatic groups.

The molecular weight of R4 preferably is less than 300 Da.

Preferably, the compound according to formula (I) has a molecular weight lower than 500 Da.

Preferably, the compound according to formula (I) does not comprise an aromatic heterocyclic ring.

Preferably, R4 comprises a carbonyl group, and most preferably, a carbonyl group attached to the trolox moiety.

In one preferred embodiment, R4 is —CO—N—R5, wherein the C═O is bound to the trolox moiety, and wherein R5 is an alkylgroup, optionally substituted with nitrogen or oxygen, wherein the alkylgroup comprises 1-12 carbon atoms, and wherein nitrogen can be amine, quaternary amine, guanidine or imine, and oxygen can be hydroxyl, carbonyl or carboxylic acid. Oxygen and nitrogen together may form amide, urea or carbamate groups.

The alkylgroup in R5 may be linear, branched or cyclic, and preferably comprises at least one cyclic structure.

Compounds as presented by formula (I) can be made according to known chemical synthesis.

For example, compounds with a guanidine group, or a piperazine group attached to a trolox moiety via an alkyl group are described in EP202580. Analogous synthesis can be used, wherein the 6-oxygen is protected, and liberated after the synthesis, or protected with a prodrug-moiety.

For example, compounds with nicotinate groups as substituents, are described in U.S. Pat. No. 461,890. The nicotinate attached to the 6-oxygen of the trolox moiety can act as a prodrug moiety, which is hydrolysed in vivo to a free hydroxylgroup.

For example, suitable compounds are described in WO88/08424, examples 18-23 and 78-164.

For example, suitable compounds are described in WO97/41121, in preparations 1, 6, 7, 12-15, 21, 24 and 27, wherein the benzoylgroup can be removed, or can act as a prodrug moiety.

Further compounds are described in e.g. WO03/024943, like compounds 9-11, 25-28, 109-112, 119-122 etc.

For example, compounds having a quaternary ammonium group are described in WO2014/011047, including a description of synthesis in the examples.

The compounds of the present invention are unexpectedly active against chronic obstructive airway diseases such as COPD or asthma.

The compounds according to the present invention preferably have a Trolox oxidation equivalent, which is comparable or less than trolox, but their activity in preventing cell-damage is substantially improved.

Considering that the present compounds target the lungs, inhalation is the most preferred administration route to be used in the present treatment of chronic obstructive airway diseases, such as chronic obstructive pulmonary disease (COPD) or asthma or bronchiectasis, and especially chronic obstructive pulmonary disease (COPD). Inhaled compounds can be absorbed quickly, and can act both locally and systemically. Because proper techniques with inhaler devices is necessary to achieve the correct dose, the present invention, according to a further aspect, relates drug delivery device wherein the device is an inhaler such as a nebulizer comprising the present compounds, and comprising the active ingredient or a pharmaceutically acceptable salt or base thereof in a formulation suitable for inhalation.

An inhaler, or puffer, is a medical device used for delivering medication into the body via the lungs. An inhaler is generally used in the treatment of asthma and Chronic Obstructive Pulmonary Disease (COPD). To reduce deposition in the mouth and throat, and to reduce the need for precise synchronization of the start of inhalation with actuation of the device, MDIs are sometimes used with a complementary spacer or holding chamber device. Types of inhalers are metered-dose inhalers, dry powder inhalers and nebulizers.

The most common type of inhaler is the pressurized metered-dose inhaler (MDI). In MDIs, medication is most commonly stored in solution in a pressurized canister that contains a propellant, although it may also be a suspension. The MDI canister is attached to a plastic, hand-operated actuator. On activation, the metered-dose inhaler releases a fixed dose of medication in aerosol form. The aerosolized medication is drawn into the lungs by continuing to inhale deeply before holding the breath for approximately 10 seconds to allow the aerosol to settle onto the walls of the bronchial and other airways of the lung.

Dry powder inhalers or DPI release a metered or device-measured dose of powdered medication that is inhaled through a DPI device. Nebulizers supply the medication as an aerosol created from an aqueous formulation.

The compound according the invention is formulated such that it is suitable for inhalation. In a preferred embodiment, the aerodynamic diameter of the drug is in the range of 0.5-8 μm, more preferably in the 1-5 μm aerodynamic diameter range. In this range, the drug is most efficiently absorbed, because it relates to particle dynamic behavior and describes the main mechanisms of aerosol deposition; both gravitational settling and inertial impaction depend on aerodynamic diameter. The formulation may further comprise excipients, although this is not necessary. Suitable excipients include lactose, glucose and mannitol, of which lactose is preferred.

Preparing a drug for inhalation is known, as for example described in Respiratory Care (2005) 50: 1209-1227. For MDI, a propellant will be present, and optionally a surfactant.

The amount of compound according to the present invention to be administered per actuation of an inhaler is about 1 mmol or less, preferably about 0.3 mmol or less. The molecular weight of the compound being generally below 400 g/mol, this means that the amount to be administered per actuation is about 200 mg or less, preferably about 100 mg or less. Generally, the amount of compound according the present invention is 1 μmol or more, preferably about 10 μmol or more. Generally, the amount of compound will be about 100 μg or more.

The compound of the present invention can be combined with other known treatments of asthma or COPD, such as described above. In particular, the compound of the present invention may be combined with corticosteroids and/or long-acting or short-acting β3-agonists and/or leukotrienes. The combination therapy may be effected in the same inhaler, or in multiple inhalers.

The present invention will be further illustrated using the examples below. In the examples, reference is made to figures wherein FIG. 1: shows that SUL-compounds do not alter cell viability. hTERT cells were incubated for 24 hours with the indicated concentrations of SUL90, SUL121, SUL127 and SUL136 in the absence of presence of 15% CSE. The H2S donor NaSH (500 μM) served as control. Data are expressed as mean±SEM, n=4-5, *p<0.05 vs. control in one-way ANOVA followed by Benferroni post hoc test;

FIG. 2: shows that Sul-90 and Sul-121 inhibit CSE-induced IL-8 release from hTERT cells. hTERT cells were incubated for 24 hours with the indicated concentrations of Sul-90 and Sul-121 in the absence of presence of 15% CSE. The β2-agonist fenoterol (Feno, 1 μM) and the $H_2S$ donor NaSH (500 μM) served as controls. Data are expressed as mean±SEM, n=4-5, *p<0.05 vs. control in one-way ANOVA followed by Benferroni post hoc test;

FIG. 3 shows that Sul-90 and Sul-121 induce relaxation of methacholine-pre-contracted BTSM strips. The upper panel illustrates the protocol of the isometric tension measurements. BTSM strips were pre-contracted with 1×10−3.5 μM methacholine, followed by the addition of the indicated concentrations of the Sul-compounds. DMSO (0.5%) served as control. Graphs represent means±SEM of 6 experiments. *p<0.05 vs. control in two-way ANOVA;

FIG. 4: shows that the β2-adrenoceptor antagonist propranolol does not alter the relaxation of BTSM strips induced by Sul-90 and Sul-121. BTSM strips were pre-contracted with 1×10−3.5 μM methacholine, followed by the addition of Sul-90 and Sul-121 (30 μM each) in the presence and absence of 1 μM propranolol. Graphs represent means±SEM of 3 experiments. *p<0.05 vs. control in two-way ANOVA;

FIG. 5: shows that Sul-121, but not Sul-90, shifts the dose response curve for isoprenaline to the right. BTSM strips were pre-contracted with 1×10−3.5 μM methacholine, followed by the addition of Sul-90 and Sul-121 (30 μM each) followed by a dose response curve for isoprenaline. DMSO (0.03%) served as control. Graphs represent means±SEM of 3 experiments. *p<0.05 vs. control in two-way ANOVA;

FIG. 6: shows that Sul-121 and Sul-90 decrease the contraction induced by methacholine. BTSM strips were pre-incubated with Sul-90 and Sul-121 (30 μM each), followed by a dose response curve for methacholine. DMSO (0.03%) served as control. Graphs represent means±SEM of 3 experiments. *p<0.05 vs. control in two-way ANOVA.

FIG. 7 shows the effect of Sul-121 on airway hyperresponsiveness after LPS challenging.

EXAMPLES

Example 1: Synthesis of Several Compounds

Figure 1:
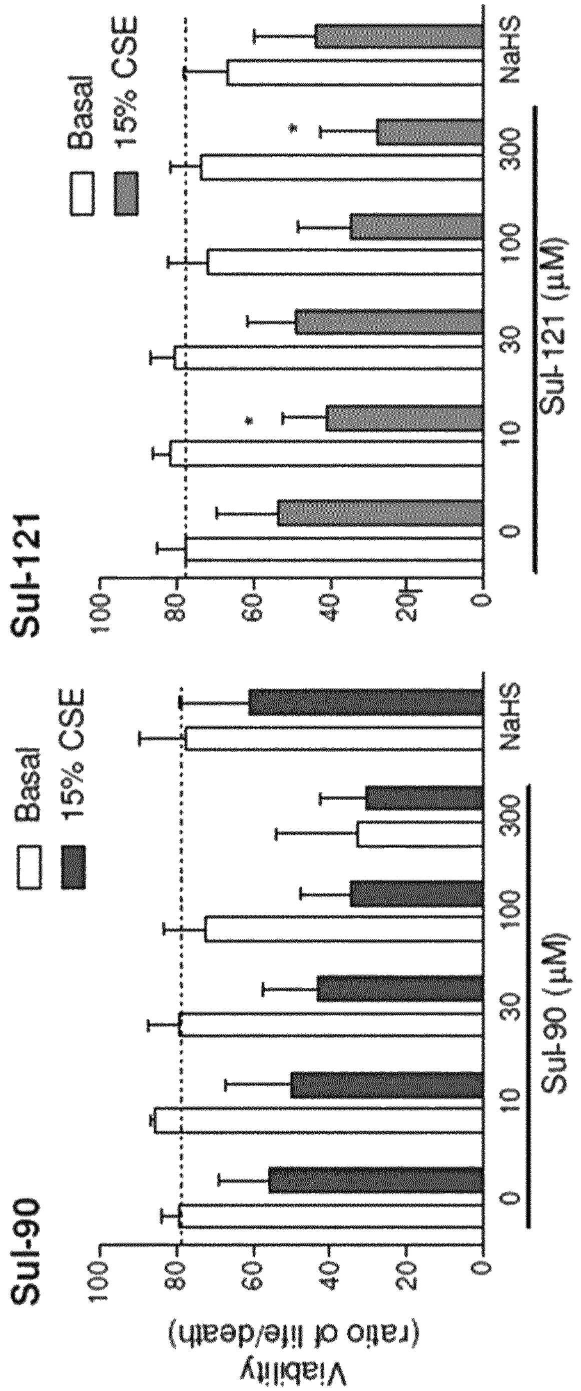

Compounds according to the invention can be synthesized according to standard synthesis methods which are well known by a person skilled in the art. SUL-0083, SUL-0084 and SUL-0085 are commercially available. Table 1 below provides a summary of the present compounds as an interchangeable arbitrary indication (code) of the present compounds used herein.

TABLE 1

Several compounds according to the present invention

| Code | Chemical name |
|---|---|
| SUL-083 | 2,2,5,7,8-pentamethylchroman-6-ol |
| SUL-084 | (S)-6-hydroxy-2,5,7,8-tetramethylchroman-2-carboxylic acid |
| SUL-085 | (R)-6-hydroxy-2,5,7,8-tetramethylchroman-2-carboxylic acid |
| SUL-089 | 6-hydroxy-2,5,7,8-tetramethylchroman-2-carboxamide |
| SUL-090 | N,6-dihydroxy-2,5,7,8-tetramethylchroman-2-carboxamide; |
| SUL-091 | N-butyl-6-hydroxy-2,5,7,8-tetramethylchroman-2-carboxamide; |
| SUL-092 | 6-hydroxy-N-isopropyl-2,5,7,8-tetramethylchroman-2-carboxamide; |
| SUL-093 | (E)-N-(3,7-dimethylocta-2,6-dien-1-yl)-6-hydroxy-2,5,7,8-tetramethylchroman-2-carboxamide; |
| SUL-095 | (6-hydroxy-2,5,7,8-tetramethylchroman-2-yl)(morpholino)methanone; |
| SUL-097 | N-(4-fluorobenzyl)-6-hydroxy-2,5,7,8-tetramethylchroman-2-carboxamide; |
| SUL-098 | 6-hydroxy-N-((S)-2-hydroxy-1-phenylethyl)-2,5,7,8-tetramethylchroman-2-carboxamide; |
| SUL-100 | 6-hydroxy-2,5,7,8-tetramethyl-N-(2-(methylamino)ethyl)chroman-2-carboxamide; |
| SUL-101 | 6-hydroxy-N,2,5,7,8-pentamethyl-N-(2-(methylamino)ethyl)chroman-2-carboxamide; |
| SUL-102 | 6-hydroxy-2,5,7,8-tetramethyl-N-(3-(piperidin-1-yl)propyl)chroman-2-carboxamide; |
| SUL-104 | 6-hydroxy-2,5,7,8-tetramethyl-N-(3-nitrophenyl)chroman-2-carboxamide; |
| SUL-106 | N-(4-fluorophenyl)-6-hydroxy-2,5,7,8-tetramethylchroman-2-carboxamide; |
| SUL-107 | methyl 4-(6-hydroxy-2,5,7,8-tetramethylchroman-2-carboxamido)benzoate; |
| SUL-108 | (4-butylpiperazin-1-yl)(6-hydroxy-2,5,7,8-tetramethylchroman-2-yl)methanone; |
| SUL-109 | (6-hydroxy-2,5,7,8-tetramethylchroman-2-yl)(4-(2-hydroxyethyl)piperazin-1-yl)methanone; |
| SUL-110 | ((2S,5R)-4-allyl-2,5-dimethylpiperazin-1-yl)(6-hydroxy-2,5,7,8-tetramethylchroman-2-yl)methanone; |
| SUL-111 | N-((R)-2-amino-2-oxo-1-phenylethyl)-6-hydroxy-2,5,7,8-tetramethylchroman-2-carboxamide; |
| SUL-112 | (6-hydroxy-2,5,7,8-tetramethylchroman-2-yl)((S)-2-(hydroxymethyl)pyrrolidin-1-yl)methanone; |
| SUL-114 | N-(2-bromoethyl)-6-hydroxy-2,5,7,8-tetramethylchroman-2-carboxamide; |
| SUL-115 | N'-(2-cyanoethyl)-6-hydroxy-2,5,7,8-tetramethylchroman-2-carbohydrazide; |
| SUL-116 | 2-(((4-fluorobenzyl)amino)methyl)-2,5,7,8-tetramethylchroman-6-ol; |
| SUL-117 | 2-((butylamino)methyl)-2,5,7,8-tetramethylchroman-6-ol; |
| SUL-118 | 6-hydroxy-5,7-diisopropyl-2,8-dimethylchroman-2-carboxylic acid; |
| SUL-119 | 2-(hydroxymethyl)-5,7-diisopropyl-2,8-dimethylchroman-6-ol; |
| SUL-120 | 6-hydroxy-N-((R)-1-hydroxypropan-2-yl)-2,5,7,8-tetramethylchroman-2-carboxamide |
| SUL-121 | (6-hydroxy-2,5,7,8-tetramethylchroman-2-yl)(piperazin-1-yl)methanone |
| SUL-122 | (6-hydroxy-2,5,7,8-tetramethylchroman-2-yl)(4-(2-(2-hydroxyethoxy)ethyl)piperazin-1-yl)methanone; |
| SUL-123 | N-(2-cyanoethyl)-6-hydroxy-2,5,7,8-tetramethylchroman-2-carboxamide; |
| SUL-124 | 6-hydroxy-N-(2-((2-hydroxyethyl)(methyl)amino)ethyl)-2,5,7,8-tetramethylchroman-2-carboxamide; |
| SUL-125 | (R)-N,6-dihydroxy-2,5,7,8-tetramethylchroman-2-carboxamide; |
| SUL-126 | (S)-N,6-dihydroxy-2,5,7,8-tetramethylchroman-2-carboxamide; |
| SUL-128 | 2-(((S)-2-(hydroxymethyl)pyrrolidin-1-yl)methyl)-2,5,7,8-tetramethylchroman-6-ol; |
| SUL-129 | 2-((((S)-2-hydroxy-1-phenylethyl)amino)methyl)-2,5,7,8-tetramethylchroman-6-ol; |
| SUL-130 | 2,5,7,8-tetramethyl-2-(piperidin-1-ylmethyl)chroman-6-ol; |
| SUL-131 | N,6-dihydroxy-5,7-diisopropyl-2,8-dimethylchroman-2-carboxamide; |
| SUL-132 | (6-hydroxy-2,5,7,8-tetramethylchroman-2-yl)(4-(2-hydroxyethyl)piperazin-1-yl)methanone; |
| SUL-133 | (6-hydroxy-5,7-diisopropyl-2,8-dimethylchroman-2-yl)(4-(2-hydroxyethyl)piperazin-1-yl)methanone; |
| SUL-134 | 2-(((S)-2-(hydroxymethyl)pyrrolidin-1-yl)methyl)-2,5,7,8-tetramethylchroman-6-ol; |
| SUL-135 | 2-(((S)-2-(hydroxymethyl)pyrrolidin-1-yl)methyl)-2,5,7,8-tetramethylchroman-6-ol; |
| SUL-136 | 2-(4-(6-hydroxy-2,5,7,8-tetramethylchroman-2-carbonyl)piperazin-1-yl)acetic acid; |
| SUL-137 | (6-hydroxy-5,7-diisopropyl-2,8-dimethylchroman-2-yl)(piperazin-1-yl)methanone; |
| SUL 138 | (6-hydroxy-2,5,7,8-tetramethylchroman-2-yl)(4-(2-hydroxyethyl)piperazin-1-yl)methanone; |
| SUL-139 | 2-(4-(6-hydroxy-5,7-diisopropyl-2,8-dimethylchroman-2-carbonyl)piperazin-1-yl)acetic acid; |
| SUL-140 | ethyl 2-(4-(6-hydroxy-2,5,7,8-tetramethylchroman-2-carbonyl)piperazin-1-yl)acetate; |
| SUL-141 | (S)-2-(4-(6-hydroxy-2,5,7,8-tetramethylchroman-2-carbonyl)piperazin-1-yl)acetic acid; |
| SUL-142 | (R)-2-(4-(6-hydroxy-2,5,7,8-tetramethylchroman-2-carbonyl)piperazin-1-yl)acetic acid; |

TABLE 1-continued

| Several compounds according to the present invention | |
|---|---|
| Code | Chemical name |
| SUL-143 | (2S)-1-(6-hydroxy-2,5,7,8-tetramethylchroman-2-carbonyl)pyrrolidine-2-carboxylic acid; |
| SUL-144 | (2S)-1-(6-hydroxy-2,5,7,8-tetramethylchroman-2-carbonyl)pyrrolidine-2-carboxylic acid; |
| SUL-145 | (2S)-1-(6-hydroxy-2,5,7,8-tetramethylchroman-2-carbonyl)pyrrolidine-2-carboxylic acid; |

Synthesis of SUL 089-112, 114-117, 120-126, 128-130, 132, 134-135, 138, and 140

Amidation of trolox was achieved by reaction with the appropriate amine in the presence of standard coupling reagents for amide formation, e.g., HATU and CDI. The corresponding amines were prepared by reduction of the amides formed with $BH_3$ Hydroxamic acid derivatives were prepared by reaction with hydroxylamine/CDI. The synthesis of carbohydrazide analogues of trolox was achieved by reaction with (substituted) hydrazines. Enantiomeric/diastereomeric compounds were prepared starting from enantiomerically pure (R)- or (S)-Trolox or by means of chiral chromatography.

Synthesis of SUL-118, SUL-119 en SUL-146

Oxidation of commercially available propofol with salcomine, a coordination complex of the salen ligand with cobalt, followed by reduction with $NaBH_4$ afforded 2,6-diisopropylbenzene-1,4-diol Subsequent methylation with $HCO/SnCl_2/HCl$ and reaction with methyl methacrylate furnished SUL-146 (methyl 6-hydroxy-5,7-diisopropyl-2,8-dimethylchroman-2-carboxylate). Hydrolysis with LiOH yielded the carboxylic acid SUL-118 (6-hydroxy-5,7-diisopropyl-2,8-dimethylchroman-2-carboxylic acid). The alcohol SUL-119 (2-(hydroxymethyl)-5,7-diisopropyl-2,8-dimethylchroman-6-ol) was obtained by reduction of SUL-146 with $LiAlH_4$.

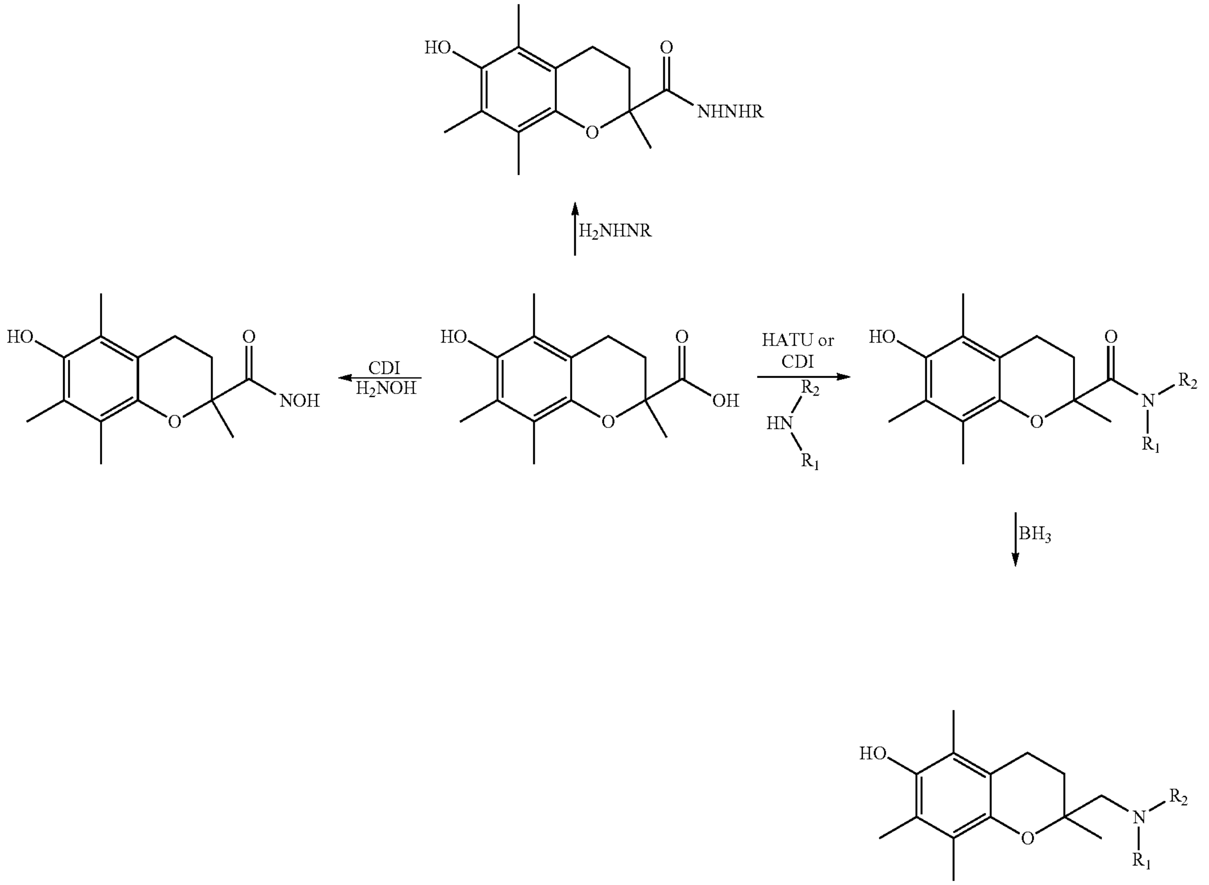

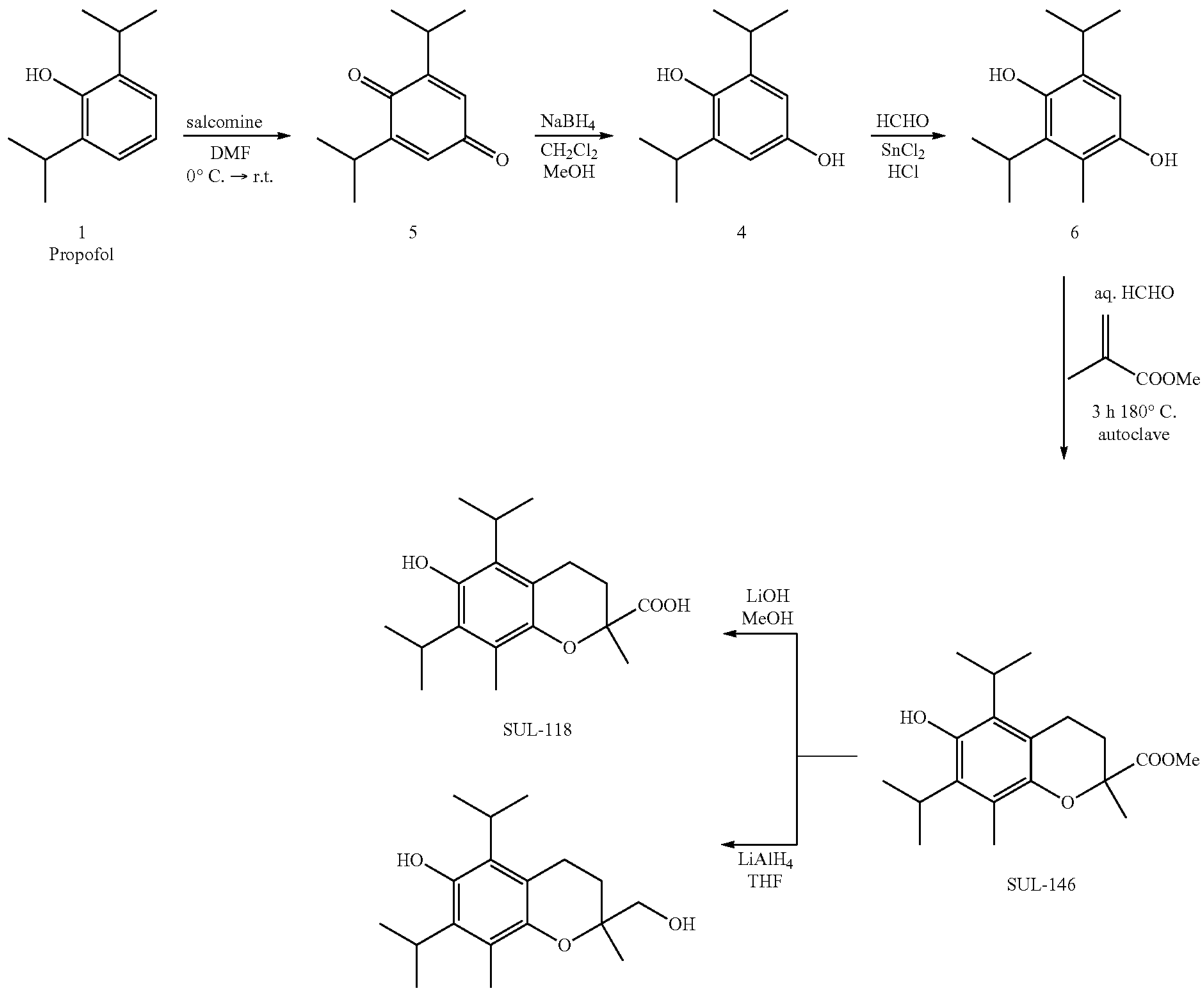

1 Propofol; 5; 4; 6; SUL-118; SUL-146; SUL-119

Synthesis of SUL-131, SUL-133, SUL 137 en SUL-146

Starting from the carboxylic acid SUL-118 (6-hydroxy-5,7-diisopropyl-2,8-dimethylchroman-2-carboxylic acid), the hydroxylamine was obtained by reaction with hydroxylamine using CDI as coupling reagent. Compounds SUL 133 ((6-hydroxy-5,7-diisopropyl-2,8-dimethylchroman-2-yl)(4-(2-hydroxyethyl)piperazin-1-yl)methanone) and SUL 137 ((6-hydroxy-5,7-diisopropyl-2,8-dimethylchroman-2-yl)(piperazin-1-yl)methanone) were prepared by reaction of SUL-118 with the appropriate piperazine derivative. Both coupling reagents HATU and CDI resulted in satisfactorily yields. SUL 139 (2-(4-(6-hydroxy-5,7-diisopropyl-2,8-dimethylchroman-2-carbonyl)piperazin-1-yl)acetic acid) was prepared by a reductive amination of SUL 137 ((6-hydroxy-5,7-diisopropyl-2,8-dimethylchroman-2-yl)(piperazin-1-yl)methanone) with glyoxalic acid.

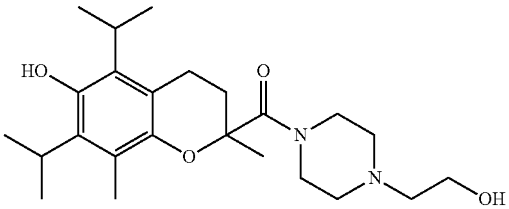

SUL-133

-continued

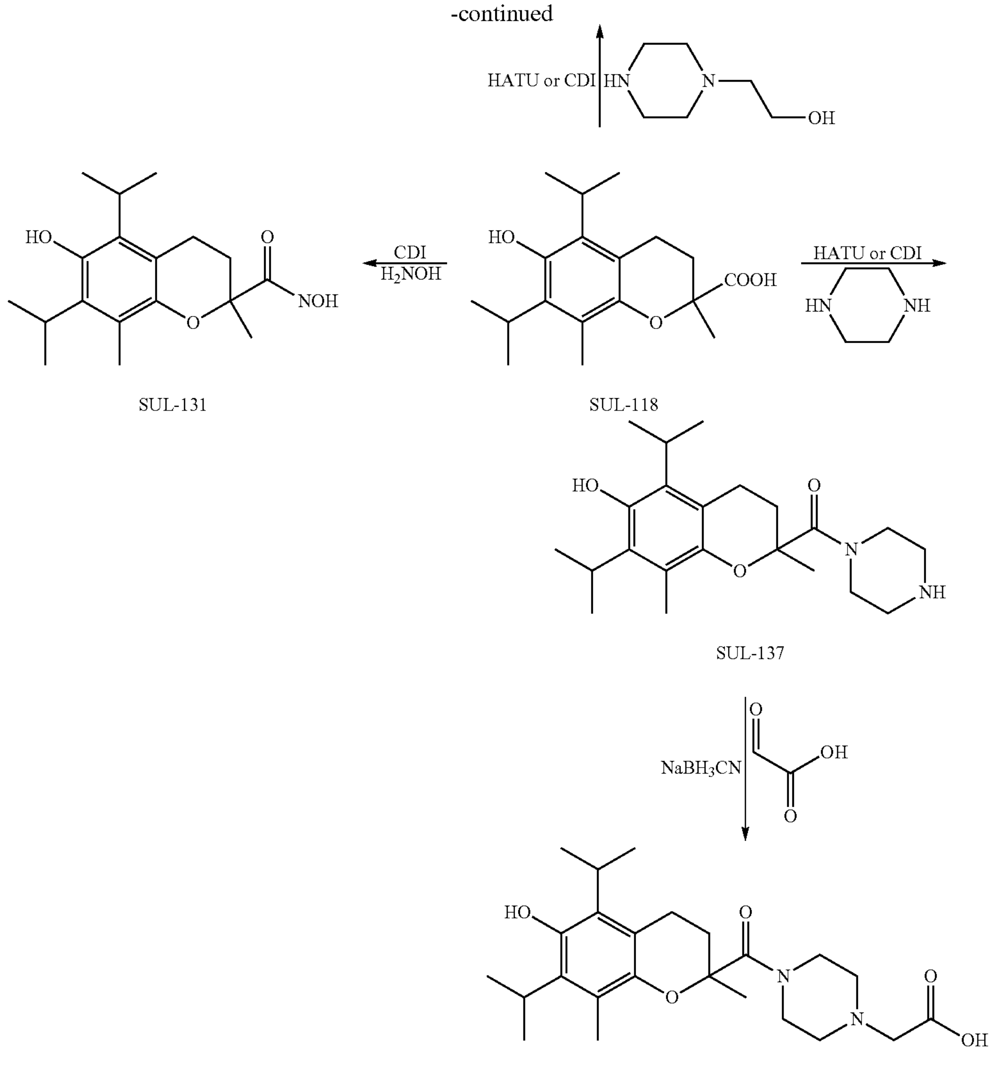

SUL-131

SUL-118

SUL-137

SUL-139

Synthesis of SUL-136, SUL-141 and SUL-142

Hydrolysis of SUL-140 (ethyl 2-(4-(6-hydroxy-2,5,7,8-tetramethylchroman-2-carbonyl)piperazin-1-yl)acetate) under $N_2$ atmosphere furnished SUL-136 (2-(4-(6-hydroxy-2,5,7,8-tetramethylchroman-2-carbonyl)piperazin-1-yl)acetic acid) in high yield. The enantiomers SUL-141 and SUL-142 were prepared according to the above-described conditions.

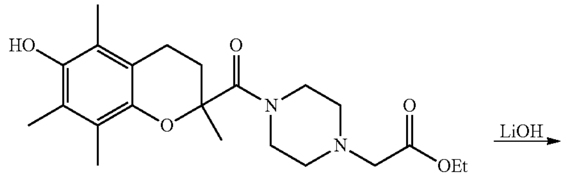

SUL-140

-continued

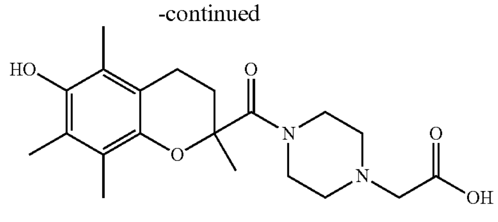

SUL-136

Synthesis of SUL 143, 144 en 145

Amidation of trolox with (S)-methyl pyrrolidine-2-carboxylate (L-proline methyl ester) afforded, after column chromatography, two diastereoisomers. Subsequent hydrolysis of the individual diastereoisomers afforded SUL-144 ((2S)-1-(6-hydroxy-2,5,7,8-tetramethylchroman-2-carbonyl)pyrrolidine-2-carboxylic acid, diastereomer 1) and SUL-145 ((2S)-1-(6-hydroxy-2,5,7,8-tetramethylchroman-2-carbonyl)pyrrolidine-2-carboxylic acid, diastereomer 2). The racemic analogue SUL-143 ((2S)-1-(6-hydroxy-2,5,7, 8-tetramethylchroman-2-carbonyl)pyrrolidine-2-carboxylic acid) was obtained by mixing the esters of the individual diastereoisomers followed by hydrolysis of the ester moiety using LiOH.

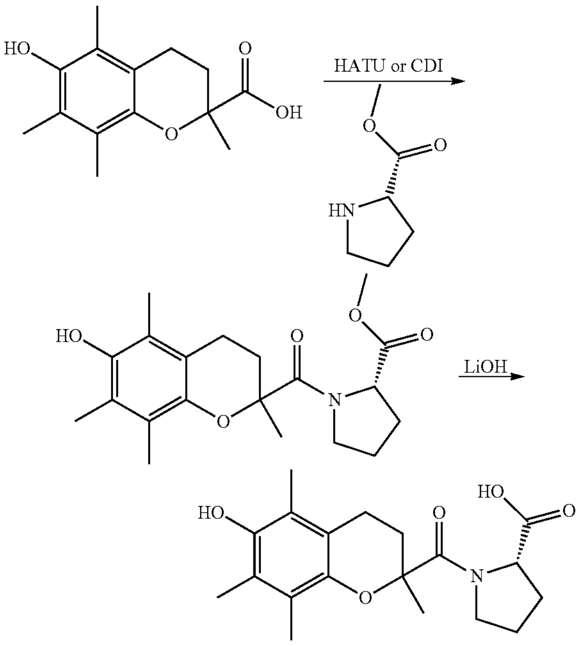

SUL-0143

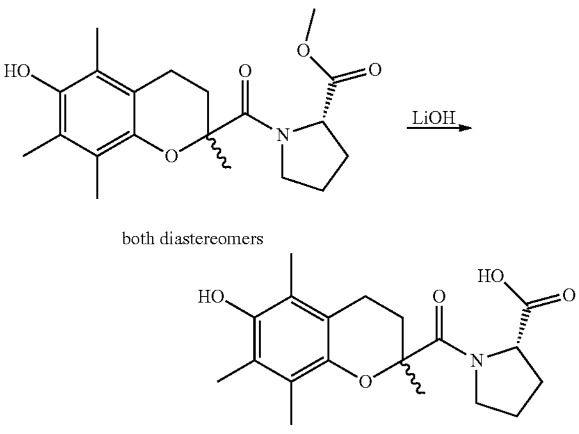

both diastereomers diastereomers SUL-0144 and SUL-145

Amidation of Trolox (General Example)

SUL-108 ((4-butylpiperazin-1-yl)(6-hydroxy-2,5,7,8-tetramethylchroman-2-yl)methanone). HCl Trolox (11 g, 0.044 mol, 1 eq.) was suspended in acetonitrile (100-150 ml). CDI (8.6 g, 0.053 mol, 1.2 eq.) was added in portions. The reaction mixture was stirred for 0.5-1 hour at room temperature. After addition of 1-butylpiperazine (6.9 g, 0.048 mol, 1.1 eq.) the reaction mixture was stirred at 25-30° C. over the weekend. The reaction mixture was concentrated, $H_2O$ (200 ml) was added and the aqueous layer was extracted with EtOAc (4×). The combined organic layers were dried, filtered and concentrated. The crude product obtained was purified by column chromatography (DCM/10% MeOH) affording the compound aimed for (9 g product, 82% pure). Crystallization from EtOAc/heptanes afforded SUL-108 (6 g, 0.016 mol, 36% yield, 90% pure) as a white solid. The material obtained was dissolved in DCM (50-100 ml). HCl (4 M in dioxane, 8.8 ml, 0.0035 mol, 2.2 eq.) was added and the reaction mixture was stirred at room temperature over the weekend. The mixture was filtered, rinsed with DCM, and dried to afford the HCl salt of SUL-108 (6.3 g, 97-98% pure) as a white solid.

$^1$H-NMR ($CDCl_3$, in ppm): 0.93 (t, 3H), 1.38 (m, 2H), 1.58 (s, 3H), 1.67 (m, 2H), 2.09 (s, 3H), 2.12 (s, 3H), 2.15 (s, 3H), 2.50-3.20 (m, 14H). $M^+$=375.3

Reduction of Trolox Amides (General Example)

SUL-128. (2-(((S)-2-(hydroxymethyl)pyrrolidin-1-yl)methyl)-2,5,7,8-tetramethylchroman-6-ol).HCl $BH_3$.THF in THF (16 ml, 0.0156 mol, 2 eq.) was cooled to T=0° C. A solution of SUL-112 ((6-hydroxy-2,5,7,8-tetramethylchroman-2-yl)((S)-2-(hydroxymethyl)pyrrolidin-1-yl)methanone; 2.6 g, 0.0078 mol, 1 eq.) in THF (50 ml) was added drop-wise and the reaction mixture was refluxed for 1 hour and cooled to room temperature overnight. The reaction mixture was cooled on an ice bath and HCl (6 M, 25 ml) was added drop-wise. DCM (100 ml) was added and the layers were separated. The aqueous layer was extracted with DCM (3×). The combined org. layers were dried over $K_2CO_3$ until no gas formation was noticed anymore. The organic phase was filtered and concentrated. The crude product was cooled on an ice bath, and NaOH (6M, 50 ml) was added drop-wise. After addition the reaction mixture was stirred for 1 hour and extracted with DCM (4×). The combined DCM layers were dried, filtered and concentrated to give 1.6 g crude product (20-40% pure). The material was purified by column chromatography affording SUL-128 (300 mg, 0.94 mmol, 12% yield, 90% pure). This was dissolved in DCM (10 ml) and cooled to T=0° C. (ice bath). HCl (4M in dioxane, 0.3 ml, 0.94 mmol, 1.2 eq.) was added and the reaction mixture was stirred at room temperature overnight. The solid formed was filtered, washed with $Et_2O$ and dried to afford the HCl salt of SUL-128 (300 mg, 90% pure) as a white solid (mixture of diastereomers).

$^1$H-NMR ($CDCl_3$, in ppm): 1.20-1.90 (m, 7H), 2.12 (s, 6H), 2.17 (s, 3H), 2.20-2.90 (m, 9H), 3.4-3.65 (m, 2H). $M^+$=320.1

Synthesis of SUL-118 (6-hydroxy-5,7-diisopropyl-2,8-dimethylchroman-2-carboxylic acid)

Synthesis of 2,6-Diisopropylcyclohexa-2,5-diene-1,4-dione

Propofol 100 g, 561 mmol) was dissolved in DMF (250 mL). The solution was cooled to 0° C. while stirring. Salcomine (16.6 g, 51 mmol; 9 mol %) was added and the resulting reaction mixture was stirred 112 h overnight while warming to room temperature. The reaction mixture was poured in water (7 L). The resulting slurry was extracted with heptanes (5×1 L). The combined organic extracts were dried with $Na_2SO_4$. Concentration of the solution under vacuum afforded the crude 2,6-diisopropylcyclohexa-2,5-diene-1,4-dione (62.5 g; 325 mmol; 58% yield) as an oil. The product was used in the next step without further purification.

Synthesis of 2,6-Diisopropylbenzene-1,4-dio

Crude 2,6-diisopropylcyclohexa-2,5-diene-1,4-dione (62.5 g, 325 mmol) was dissolved in dichloromethane (300 mL) and methanol (100 mL). The solution was cooled to 0° C. with an ice bath. Sodium borohydride (4.5 g, 182 mmol) was added in portions. After the addition was complete the reaction mixture was stirred at room temperature overnight. Acetone (150 mL) was added to quench the excess of sodium borohydride. After 30 minutes stirring 2N aq. HCl (200 mL) was added. After stirring for 45 minutes the mixture was extracted with ethyl acetate (4×400 mL). The combined organic layers were dried with $Na_2SO_4$. Concentration of the solution under vacuum afforded crude 2,6-diisopropylbenzene-1,4-diol (64 g, 330 mmol) as a red oil in quantitative yield. The product was used in the next step without further purification.

Synthesis of 3,5-Diisopropyl-2-methylbenzene-1,4-diol

A mixture of 2,6-diisopropylbenzene-1,4-diol (64 g, 0.33 mol), paraformaldehyde (9.8 g, 0.327 mol), $SnCl_2$ (217.9 g, 1.15 mol), concentrated aq. 37% HCl (0.6 L) and diisopropyl ether (2.5 L) was heated to reflux for 4 hours. After cooling to room temperature overnight the biphasic mixture was separated. The aqueous layer was extracted with TBME (2000 mL). The combined organic fractions were washed with 1N aq. HCl (1000 mL), water (1000 mL) and brine (1000 mL). The organic fractions were dried with $Na_2SO_4$ and concentrated under vacuum to give a 50:35 mixture of 3,5-diisopropyl-2-methylbenzene-1,4-diol and 2,6-diisopropyl-3,5-dimethylbenzene-1,4-diol (61 g oil) according to GCMS analysis. Purification by chromatography on silica gel (1200 mL) eluting with ethyl acetate/heptanes=97.5:2.5 (4000 mL), 95:5 (4000 mL) gave 3,5-diisopropyl-2-methylbenzene-1,4-diol 6 (16.6 g, 79.8 mmol; 24%: 83% pure) as an oil.

Synthesis of Methyl 6-hydroxy-5,7-diisopropyl-2,8-dimethylchroman-2-carboxylate 3,5-diisopropyl-2-methylbenzene-1,4-diol (10.6 g, 50.9 mmol; 83% pure) was dissolved in methyl methacrylate (20 mL, 186 mmol). The solution was transferred to a Teflon tube in a Berghof reactor. Aqueous formaldehyde (10 mL; 37% wt. solution, stabilized with 10-15% MeOH) was added and the reaction mixture was heated to 180° C. (internal temperature) in the closed reactor for 5 hours while stirring. After cooling to ca. 40° C. the reaction mixture was poured in MeOH (200 mL) and the mixture was concentrated under vacuum. Purification by chromatography on silica gel (600 mL) eluting with ethyl acetate/heptanes=95:5 (5000 mL; TLC: Rf~0.2; spot stained with iodine vapor) gave the desired pure product methyl 6-hydroxy-5,7-diisopropyl-2,8-dimethylchroman-2-carboxylate (10.0 g, 31.3 mmol, 61%).

Synthesis of 6-Hydroxy-5,7-diisopropyl-2,8-dimethylchroman-2-carboxylic acid (SUL-118)

A mixture of purified methyl 6-hydroxy-5,7-diisopropyl-2,8-dimethylchroman-2-carboxylate (8.3 g, 25.9 mmol) and lithium hydroxide monohydrate (4.3 g, 102.5 mmol; 4 eq.) in MeOH (100 mL), THF (100 mL) and water (25 mL) was heated for 30 minutes at ambient pressure while rotating with a rotary evaporator in a warm water bath at 60° C. The organic solvents were evaporated under vacuum. Water (150 mL) was added to the residue, followed by acetic acid (10 mL). A light orange mixture was obtained. Extraction with ethyl acetate (3×100 mL), drying of the combined organic fractions with $Na_2SO_4$ and concentration under vacuum gave the crude product as an orange solid. The solids were stirred with tBME (150 mL). A beige solid precipitated and an orange solution was obtained. Heptane (250 mL) was added and the mixture was stirred for 15 minutes. The mixture was filtered over a glass filter. The residual solids were washed with heptanes (2×50 mL) on the filter under suction. Drying of the solids under vacuum at 60° C. gave pure 6-hydroxy-5,7-diisopropyl-2,8-dimethylchroman-2-carboxylic acid (SUL-118) as an off-white solid (3.1 g, 10.13 mmol; 39%, 100% pure).

$^1$H-NMR ($CDCl_3$, in ppm): 1.38 (t, 12H), 1.52 (s, 3H), 1.87 (m, 1H), 2.20 (s, 3H), 2.30 (m, 1H), 3.20 (m, 1H), 3.38 (m, 1H). M+=307.10

Synthesis of SUL 119 (2-(hydroxymethyl)-5,7-diisopropyl-2,8-dimethylchroman-6-ol)

A solution of methyl 6-hydroxy-5,7-diisopropyl-2,8-dimethylchroman-2-carboxylate (500 mg, 1.56 mmol) in THF (12 mL) was added over 5 minutes with a syringe via a rubber septum to $LiAlH_4$ (238 mg, 6.26 mmol; 4 eq.), pre-weighed in a dry 3-mecked 100 mL roundbottomed flask under inert nitrogen atmosphere while stirring at room temperature. The exothermic addition of the ester was accompanied with gas evolution. After the addition was complete the resulting grey suspension was heated to reflux. After 3 hours the heating was stopped and the reaction was quenched by dropwise addition of EtOAc (6 mL; exothermic). Water (5 mL) was added in small portions, followed by 2N HCl (2 mL) followed by EtOAc (25 mL). The mixture was poured on $Na_2SO_4$ (ca. 50 g) and the slightly yellow organic layer was separated from the two-phase mixture. The aqueous phase was washed with EtOAc (50 mL) and the combined organic fractions were concentrated under vacuum to give the crude alcohol (530 mg) as a clear oil. Heptane (100 mL) was added and after concentration under vacuum the 2-(hydroxymethyl)-5,7-diisopropyl-2,8-dimethylchroman-6-ol (248 mg, 0.85 mmol, 54%, LCMS: 95.5% pure). M+=293.2

Synthesis of SUL 139 (2-(4-(6-hydroxy-5,7-diisopropyl-2,8-dimethylchroman-2-carbonyl)piperazin-1-yl)acetic acid SUL-137 (440 mg, 1.17 mmol, 1 eq.,) was dissolved in MeOH (50 ml) and glyoxalic acid (216 mg, 2.35 mmol, 2 eq.) was added. The resulting mixture was stirred for 1 hour at room temperature and, subsequently, $NaBH_3CN$ (183 mg, 2.94 mmol, 2.5 eq.) was added. The reaction mixture was stirred at room temperature overnight. Acetic acid (few ml) was added and after stirring at room temperature for 0.5-1 hour, the reaction mixture was concentrated. The residue obtained was dissolved in EtOAc, washed with $H_2O$ (2×), dried, filtered and concentrated to afford SUL-139 (500 mg, 1.16 mmol, 98%, 91-92% pure) as a light yellow solid.

$^1$H-NMR ($CD_3OD$, in ppm): 1.33 (dd, 12H), 1.59 (s, 3H), 1.62 (m, 1H), 2.09 (s, 3H), 2-5-3.0 (m, 7H), 3.1-3.6 (m, 4H), 3.81 (bs, 2H), 4.28 (bs, 2H). $M^+$=433.2.

Synthesis of SUL 136 (2-(4-(6-hydroxy-2,5,7,8-tetramethylchroman-2-carbonyl) piperazin-1-yl) acetic acid)

A 250 ml three-necked flask equipped with two septa (left and right) and a stopcock was charged with SUL-136 (15.5 g, 38.4 mmol) and THF/water (240 ml THF+80 ml water). The clear solution was stirred and degassed for at least 30 minutes by argon-bubbling, using an inlet tube equipped with a long syringe needle through the left septum; the right septum was equipped with a short needle and functioned as outlet. The degassed solution (which was maintained under argon) was cooled to 0° C. in an ice-bath and solid anhydrous LiOH (2.3 g, 96 mmol, 2.5 eq.) was added in one portion. The resulting reaction mixture was stirred for 2 hours at 0° C. after which it was neutralized by addition of a MeOH/water (3/1, v/v) slurry of Dowex-50WX8-200 ion-exchange resin; the final pH was approx 6. The Dowex resin was filtered off with suction and rinsed with 3 portions of MeOH/water (3/1, v/v). The filtrate was reduced in vacuo and to the wet product was added approx. 100 ml water. The resulting white aqueous suspension was freeze-dried overnight to afford SUL-136 (13.48 g, 93%. LCMS: 99.6%) as a white solid.

1H-NMR (CD3OD, in ppm)): 1.60 (s, 3H), 1.65 (m, 1H), 2.05 (s, 3H), 2.10 (s, 6H), 2.55 (m, 2H), 2.62 (m, 1H), 3.0, (bs, 4H), 3.40 (bs, 2H), 3.65 (bs, 2H), 4.25 (bs, 2H). M+=377.1

Synthesis of SUL 144 ((2S)-1-(6-hydroxy-2,5,7,8-tetramethylchroman-2-carbonyl)pyrrolidine-2-carboxylic acid)

(2S)-methyl 1-(6-hydroxy-2,5,7,8-tetramethylchroman-2-carbonyl)pyrrolidine-2-carboxylate (diastereomer 1, 3.5 g, 9.7 mmol) was dissolved in THF/$H_2O$ (60/20 mL). $N_2$ was bubbled through the solution for 1 h. The mixture was cooled in an ice-bath and LiOH.$H_2O$ (1.01 g, 24.2 mmol, 2.5 eq.) was added. The reaction mixture was stirred under $N_2$ at RT overnight. Dowex-50WX8-200 (washed 4× with MeOH/$H_2O$ 3:1) was added as a slurry in MeOH/$H_2O$ (3:1) until the pH=6. The mixture was filtered, washed with MeOH/$H_2O$ (3:1) and concentrated in vacuo. Demi $H_2O$ (50 mL) was added to the concentrate and the solution was freeze dried affording SUL-144 (3.4 g, 9.7 mmol, quant, 99.7% pure) as a off-white foam.

1H-NMR (CDCl3): 1.60 (s, 3H), 1.65-2.30 (m, 14H), 2.60 (m, 2H), 2.81 (m, 1H), 3.49 (m, 1H), 4.01 (t, 1H), 4.50 (d, 1H). M+=348.1

Example 2

Introduction $H_2S$ alters biological functions through the interplay of several distinct signaling mechanisms. Using CTH knocksout mice, the role of $H_2S$ was studied in airway hyperresponsiveness (AHR) and inflammation in a mouse of asthma. It was reported that the expression of CTH and endogenous $H_2S$ production was reduced in lungs of CTH-deficient mice compared to wild-type mice. Administration of ovalbumin to induce acute asthma reduced the CTH expression and $H_2S$ production in wild-type mice. Depletion of CTH lead to an increased AHR, airway inflammation, and elevated levels of IL-5, IL-13 and eotaxin-1 in bronchoalveolar fluid after ovalbumin challenge, features being reversed upon treatment with the $H_2S$ donor NaHS These findings clearly indicate that the CTH/H2S system plays a critical protective role in the development of asthma.

Intriguingly, there is a strong relationship between sputum and $H_2S$ levels for patients with severe asthma. Sputum $H_2S$ level represents a novel promising biomarker for obstructive lung diseases such as asthma, neutrophilic inflammation, chronic airflow obstruction and also as a reflection of β-adrenergic bronchodilator responsiveness. It has been proposed that the combined use of the β-agonist fenoterol and $H_2S$ measurements might offer a more comprehensive description of obstructive lung disease phenotypes.

In a rat model of hypoxia-induced pulmonary vascular structural changes, the $H_2S$ donor NaHS reduced the expression of the remodeling parameter collagen I, collagen III and transforming growth factor-β (TGF-β) and inhibited the proliferation of pulmonary artery smooth muscle cells. Although current studies are not yet direct related to human asthma, it is well established that the severity of asthma is worsened through an increase of airway smooth muscle mass, it is tempting to assume that TGF-β further promotes the increase in airway smooth muscle mass. A decrease in the level of TGF-β by $H_2S$ may effectively protect against processes underlying airway remodeling.

Mouse models of acute lung injury induced by combined burn and smoke inhalation, have shown that post-treatment administration of the $H_2S$ donor NaHS decreased mortality and increased median survival in mice. $H_2S$ also inhibited the level of IL-1β, but enhanced the level of the anti-inflammatory cytokine IL-10. It generally assumed that IL-10 exerts protective biological functions by suppressing the expression of adhesion molecules as well as reducing the level of macrophages and neutrophils, processes most likely involving the inhibition of the pro-inflammatory transcription factor NF-κB. Additionally, it has been proven that IL-1β exerts pro-inflammatory effects on the airway mucosal tissue. Thus, it is reasonable to propose that $H_2S$ exerts protective effects in acute lung injury through alterations in the balance of the pro-inflammatory IL-1β and the anti-inflammatory IL-10.

As outlined above, several recent disclosures indicate that $H_2S$ is of central importance in the regulation of biological functions throughout the human body. $H_2S$ dysfunction under pathophysiological circumstances of chronic obstructive pulmonary diseases, such as asthma and COPD, contributes to the progression of disease symptoms both in animal models and patients.

In this example, the effects of four $H_2S$ compounds, i.e. SUL90, SUL121 were studied on:

1) The cell viability of human (immortalized) airway smooth muscle cells (hTERT cells), 2) The release of the inflammation mediator IL-8 from hTERT cells, 3) Airway smooth muscle contractility of bovine trachea smooth muscle strips.

The samples used were:

Two SUL-compounds: SUL90, SUL121;

Human telomerase reverse transcriptase immortalized airway smooth muscles (hTERT) cells, cultured as previously described (Oldenburger et al., 2012). Prior to the experiments, cells were serum-deprived for 1 day, followed by cell treatment with the indicated concentrations of the SUL-compounds in the absence and presence of 15% cigarette smoke extract (CSE) for additional 24 hours. As controls, 1 μM fenoterol and 500 μM of the H2S donor NaHS were used.

100% cigarette smoke extract (CSE), freshly made by combusting (Watson Marlow 323 E/D, Rotterdam, The Netherlands) the smoke of two research cigarettes (University of Kentucky 2R4F) through 25 mL of DMEM (FBS-free) at a speed of approximately 1 cigarette/5 minutes. Afterwards, CSE was diluted to 15% (Oldenburger et al., 2012).

For cell-based studies, the SUL compounds were dissolved in 0.9% NaCl as 1 mM stock solutions. For the isometric tension measurements, the SUL compounds were dissolved in 100% DMSO as 100 mM stock solutions.

Assay 1: Trypan Blue Cell Counting

For cell viability measurements, trypan blue cell counting was performed as previously described (Oldenburger et al., 2012). As control, 500 μM of the $H_2S$ donor NaHS was used. Alternatively, alamar blue measurements were performed to determine cell viability essentially as described before (Oldenburger et al., 2012).

Briefly, hTERT cells were plated on 24-well plates at a cell density of 10.000 cells/well. Again cells were serum-deprived for 1 day, followed by cell treatment with the indicated concentrations of the SUL-compounds in the absence and presence of 15% cigarette smoke extract (CSE) for additional 24 hours Assay 2: Release of Interleukin-8 (IL-8) from hTERT Cells This assay was used to determine the release of interleukin-8 from hTERT cells, fenoterol (1 μM) and the $H_2S$ donor (500 μM) served as controls. 24 hours after cell stimulation with the indicated concentrations of the SUL-compounds in the absence and presence of 15% CSE, culture medium was collected to measure the IL-8 concentration in the cell supernatants according to the manufacturer's instructions (PeliKine Compact ELISA kit, Sanquin, The Netherlands), as previously described (Oldenburger et al., 2012.

Assay 3: Bovine Trachea Smooth Muscle (BTSM) Strips and Isometric Tension Measurements Isometric tension measurements were performed as described previously (Roscioni et al., 2011; Roscioni, Prins et al., 2011). BTSM strips were mounted for isometric recording in organ-baths, containing Krebs-Henseleit (KH) buffer, containing in mM: 117.5 NaCl, 25 $NaHCO_3$, 5.5 glucose, 5.6 KCl, 1.18 $MgSO_4$, 2.50 $CaCl_2$, 1.28 $NaH_2PO_4$, pre-gasses with 5% $CO_2$ and 95% $O_2$, pH 7.4. After dissection of the smooth muscle layer and careful removal of connective tissue, BTSM strips of approximately 1 cm length and 2 mm width were prepared. Tissue strips were cultured in DMEM supplemented with non-essential amino acid mixture (1:100), sodium pyruvate (1 mM), gentamicin (45 μg*ml−1), penicillin (100 U*ml−1), streptomycin 100 μg*ml−1, amphotericin B (1.5 μg*ml−1) apo-transferrin (5 μg*ml−1) and ascorbic acid (100 μM). The BTSM strips were cultured for 1-3 days before isometric tension measurement in an Innova 4000 incubator shaker 37° C., 55 rpm).

For isometric tension measurements (Roscioni et al., 2011; Roscioni, Prins et al., 2011), BTSM strips were calibrated, were mounted into the transducers and submerged into the organ baths in pre-gassed KH buffer. Each strip was adjusted to a basal tension of 3 gram. Then, the strips were washed, equilibrated again for 60 minutes, followed by pre-contractions induced by 1×10−3.5 μM methacholine. To analyze acute effects of the SUL-compounds on the isometric tension, the strips were incubated with accumulative doses of the SUL-compounds (1-300 μM), followed by the addition of 0.01 μM isoprenaline.

To analyze a potential role of the β2-AR in the effects induced by the SUL-compounds, the strips were incubated with 1 μM propranonol for 30 minutes prior addition of the SUL-compounds. To analyze potential effects of the SUL-compounds on the isoprenaline-induced relaxation, the strips were first incubated with the SUL-compounds (30 μM each), followed by the addition of accumulative doses of isoprenaline (1×10−5−1 μM). Finally, to analyze potential effects of the SUL-compounds on the methacholine-induced contraction, the strips were first incubated with the SUL-compounds (30 μM each), followed by addition of accumulative doses of methacholine (0.0001-30 μM), before the addition of 0.01 μM isoprenaline.

Data are shown as mean±standard error of the mean. One-way ANOVA followed by Bonferroni post hoc test, 2-tailed paired t-test, two-way ANOVA was used when appropriate to identify statistical differences between means. A statistical difference was defined as significant at p<0.05.

Results

SUL-Compounds on Cell Viability

As illustrated in FIG. 1, the SUL-compounds exert no significant effect on cell viability. Increasing concentrations of the SUL-compounds, however, seem to further increase the profound effect of CSE on cell viability. Shown here are cell viability studies based on trypan blue counting. Similar results were obtained using alamar blue measurements (data not shown). Thus, SUL-90 and SUL-121 seem not to severely alter the cell viability of hTERT cells.

The Effect of Sul-90, Sul-121 on the Release of IL-8 from hTERT Exposed to CSE

Figure 2:
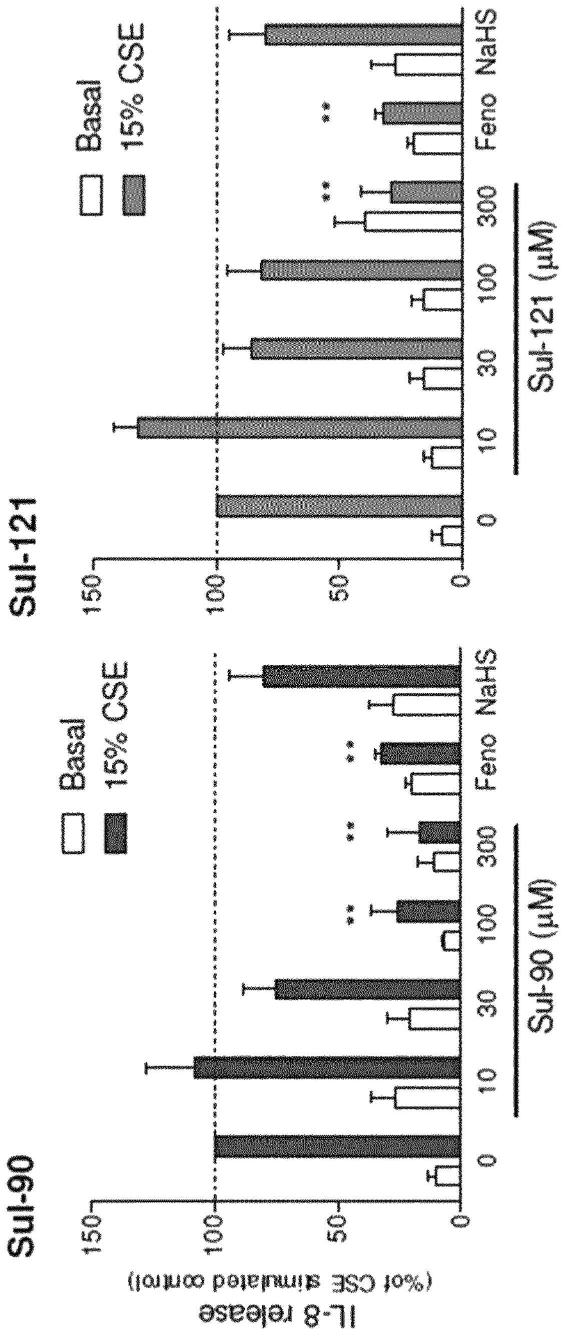
Figure 5:
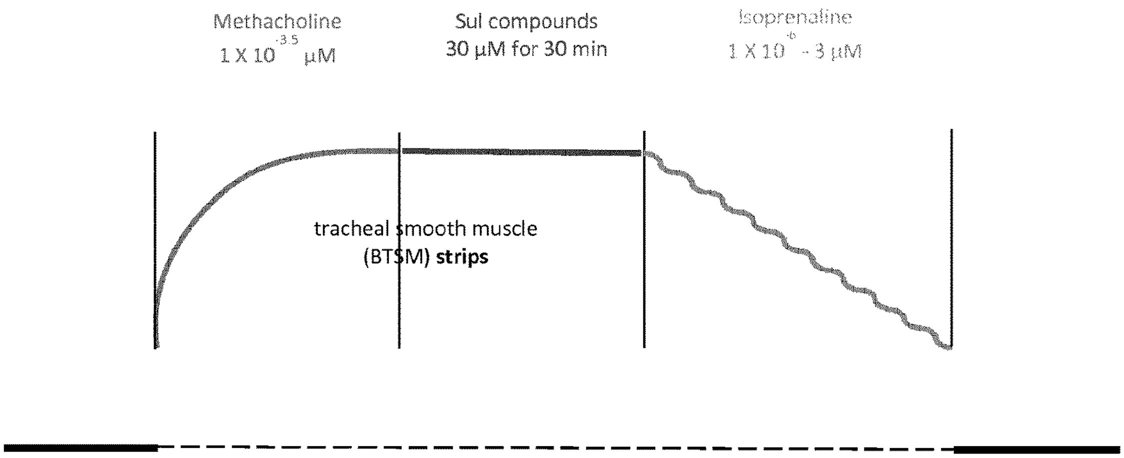
Figure 5:
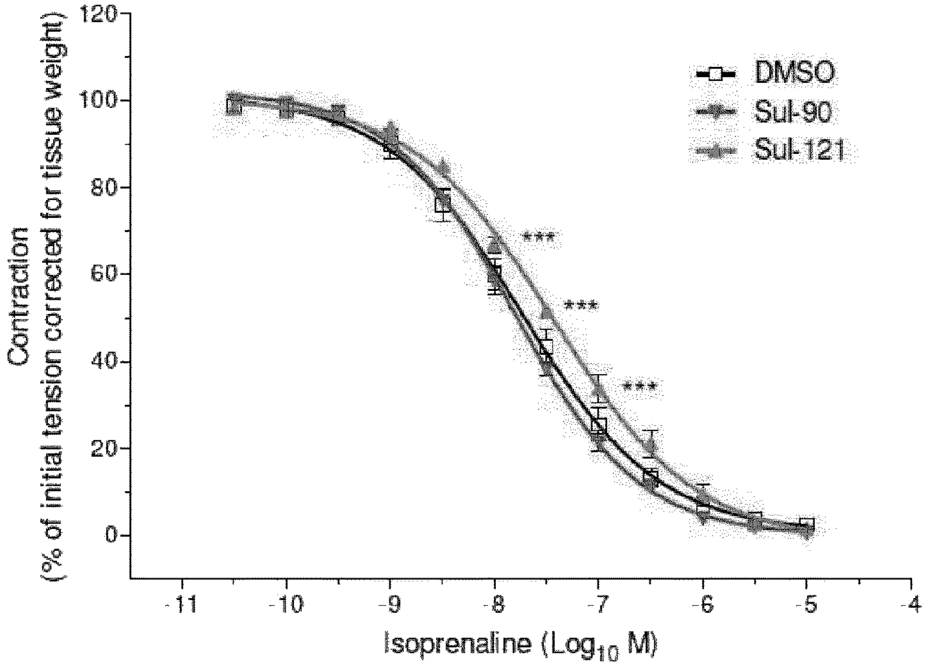

As illustrated in FIG. 2, the Sul-compounds exert differential effects on the cellular release of IL-8 induced by CSE. Sul-90 and Sul-121 significantly reduce the release of the inflammatory mediator IL-8 (FIG. 5).

Figure 3:
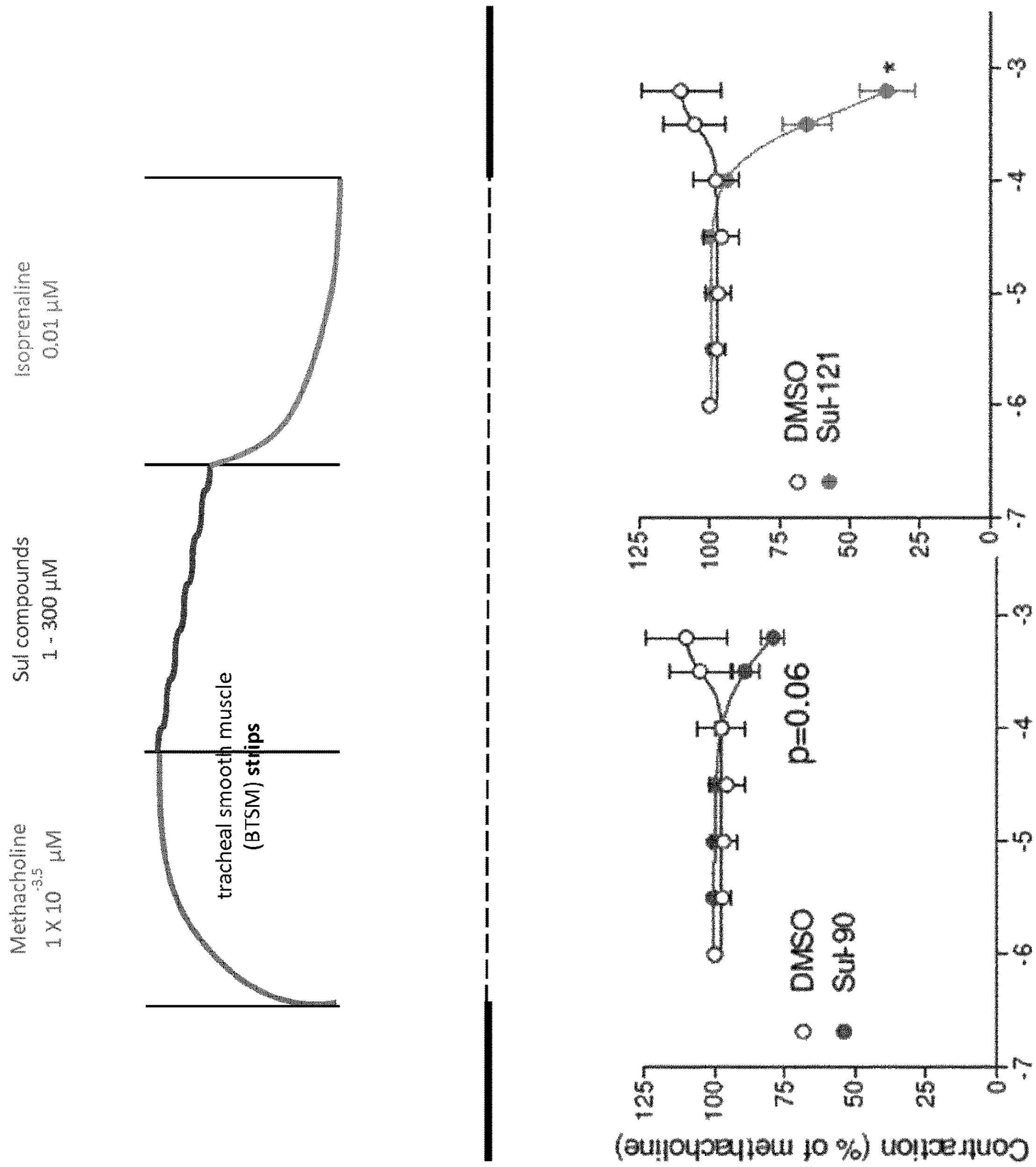

The effects of Sul-90, Sul-121, Sul-127 and Sul-136 on the Acute Relaxation of BTSM Strips As illustrated in FIG. 3, Sul-90 shows a trend to induce relaxation of BTSM strips at concentrations higher than 100 μM. Sul-121 induces even more pronounced relaxation, reaching statistical significance. In contrast, Sul-127 and Sul-136 do not alter the contractile tone of BTSM strips (FIG. 3).

The relaxation Induced by Sul-90 and Sul-121

Figure 4:
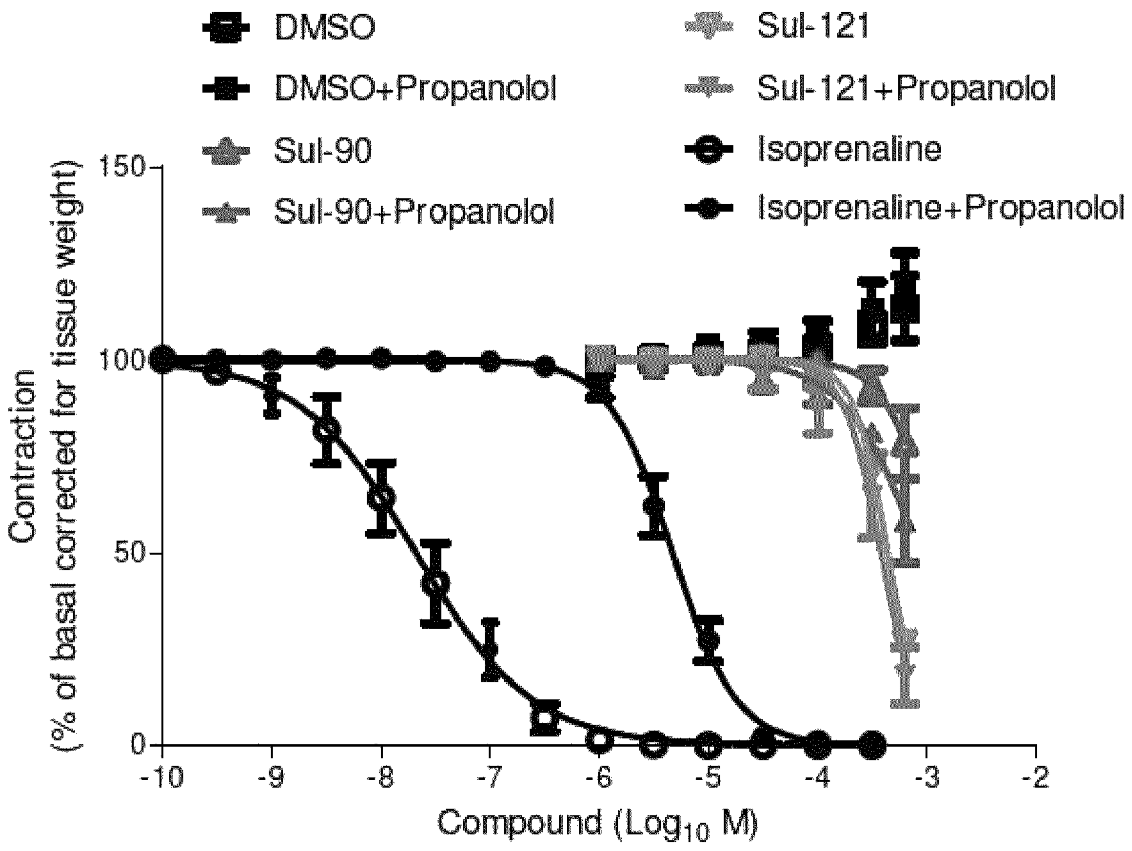

To analyze a potential involvement of the β2-adrenoceptor in their relaxing properties, the BTSM strips were pre-incubated with the β2-adrenoceptor antagonist propranolol. As illustrated in FIG. 4, propranolol induced a right-ward shift of the dose-response curve for isoprenaline. In contrast, relaxation induced by Sul90 and Sul-121 was not affected by propranolol (FIG. 4). In the presence of propranolol, Sul-90 even showed a trend to a left-ward shift of its relaxing properties. Statistical analysis (see Table 2) revealed that propranolol significantly altered the relaxation by isoprenaline, but left the relaxation induced by Sul-90 and Sul-121 unaffected. Thus, Sul90 and Sul-121 induce acute relaxation of BTSM independent of the β2-adrenoceptor.

TABLE 2

Statistical anaylsis: pD2 values were calculated from individual experimental data. Each value represented the mean ± SEM from 3 determinations. Statistical analyses were performed by a one-way ANOVA. p < 0.001 vs. all other agonists; p < 0.001 vs. solvent treated bovine tracheal smooth muscle tissue

| Agonist | Solvent | Propranolol |
|---|---|---|
| DMSO | 3.6 ± 0.1 | 3.6 ± 0.2 |
| Sul-90 | 3.4 ± 0.0 | 3.5 ± 0.0 |
| Sul-121 | 3.5 ± 0.0 | 3.5 ± 0.1 |
| Isoprenaline | 7.7 ± 0.2 | 5.4 ± 0.1 |

The Impact of Sul-90 and Sul-121 on the Isoprenaline-Induced Relaxation

The BTSM strips were pre-incubated with Sul90 and Sul-121 at a concentration of 30 μM shown before to leave the isometric tension unaffected. As illustrated in FIG. 5, Sul-121, but not Sul-90, induced a significant right-ward shift of the dose response curve for isoprenaline.

The Impact of Sul-90 and Sul-121 on the Methacholine-Induced Contraction

Figure 6:
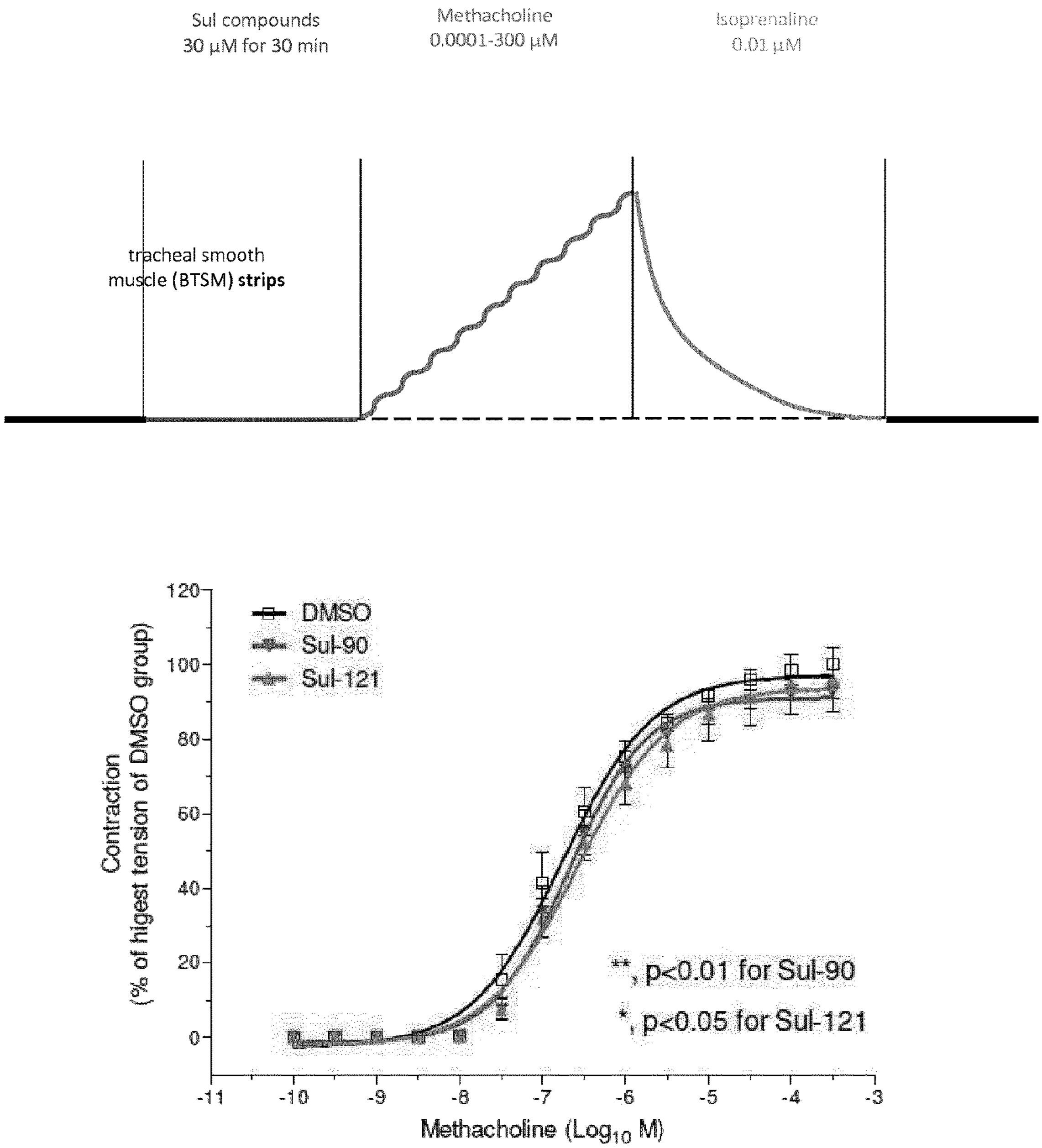

BTSM strips were pre-incubated with Sul90 and Sul-121 at a concentration of 30 μM shown before to leave the isometric tension unaffected. As illustrated in FIG. 6, Sul-90 and Sul121 reduced the contraction induced by methacholine.

Conclusions

1) SUL90 and SUL121 do not severly alter cell viability of hTERT cells.
2) SUL90 and SUL121 inhibit the cellular IL-8 release induced by CSE.
3) SUL90 and SUL121 induce relaxation of bovine trachea strips pre-contracted with methacholine in a β2-adrenoceptor-independent manner.
4) SUL212 induces a right-ward shift of the dose response curve for isoprenaline indicating that SUL121 may compete for intracellular signaling components of isoprenaline.
5) SUL90 and SUL12 significantly reduce the contraction induced by methacholine.

Example 3

Guinea pigs were instrumented with an intrapleural balloon catheter implanted for online measurement of pleural pressure. 24 hours before LPS instillation (t=–24 h), the basal airway responsiveness to histamine is measured (PC100: histamine concentration inducing a doubling of pleural pressure). 30 minutes prior to intranasal LPS instillation (t=–0.5 h), the animals were treated with saline, (6-hydroxy-2,5,7,8-tetramethylchroman-2-yl)(piperazin-1-yl)methanone or N,6-dihydroxy-2,5,7,8-tetramethylchroman-2-carboxamide or fenoterol, used as a positive control.

At time point 0 (t=0 h), LPS was instilled intranasally, after which airway hyperresponsiveness was measured at different time point (t=1, 2, 3, 6 and 24 h), by performing PC100 measurements. At t=25 h a bronchoalveolar lavage (BAL) was performed to determine the effects of the different treatments on airway inflammation. As a control for the LPS-induced effects, an intranasal challenge with saline was performed after the saline treatment at t=–0.5 h.

To assess effective doses, histamine PC100 measurements 30 min before and at various time points (30 min, 1 h, 2 h, 3 h, 6 h and 24 h) after treatment with either (6-hydroxy-2,5,7,8-tetramethylchroman-2-yl)(piperazin-1-yl)methanone or N,6-dihydroxy-2,5,7,8-tetramethylchroman-2-carboxamide were performed. Aerosol concentrations of 3, 30 and 300 mM were used for both compounds.

Under complete anaesthesia, an intrapleural balloon catheter was surgically implanted in the pleural cavity for online measurement of pleural pressure in freely moving animals. After one week of recovery, the animals were trained to adapt to the measuring method.

Figure 7:
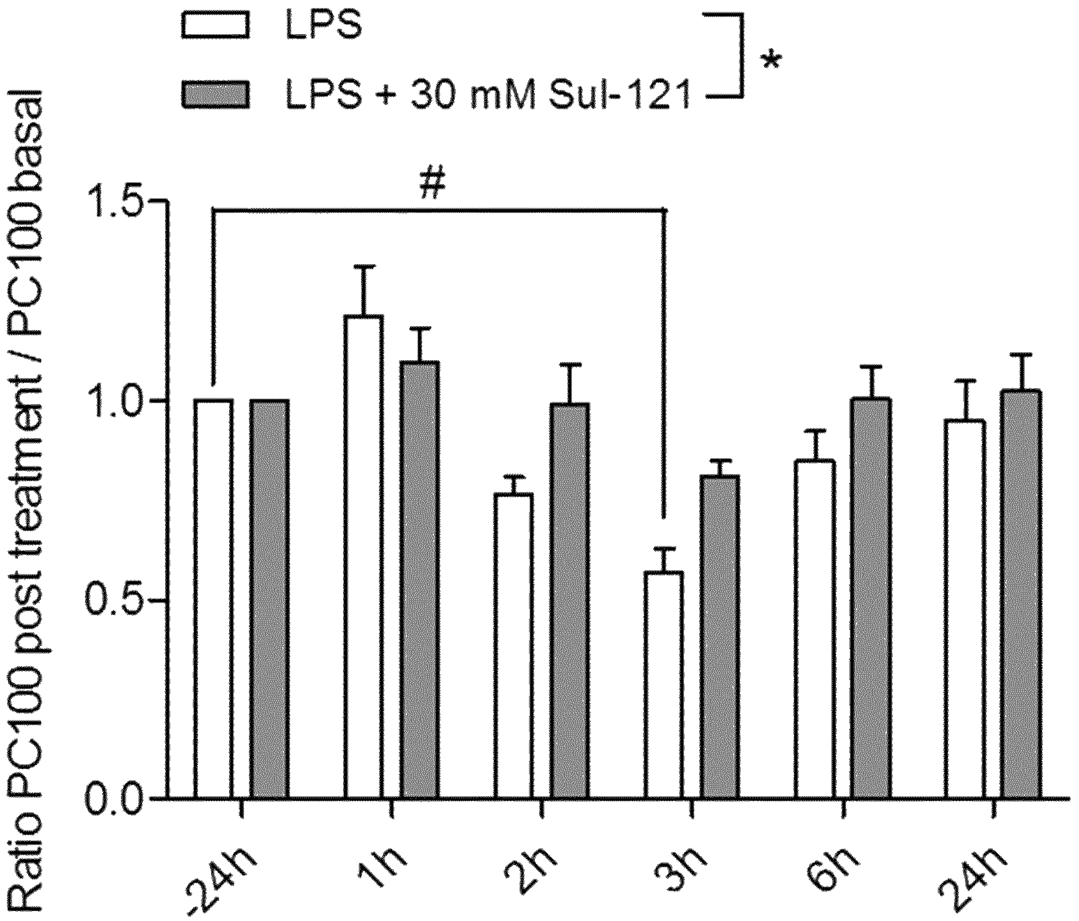
FIG. 7 shows that experiments in guinea pigs have been performed as described in Example 3.

FIG. 7 shows the effect of a compound of the present invention on airway responsiveness, and the results show that the compound has an apparent diletating effect.

Figure 8:
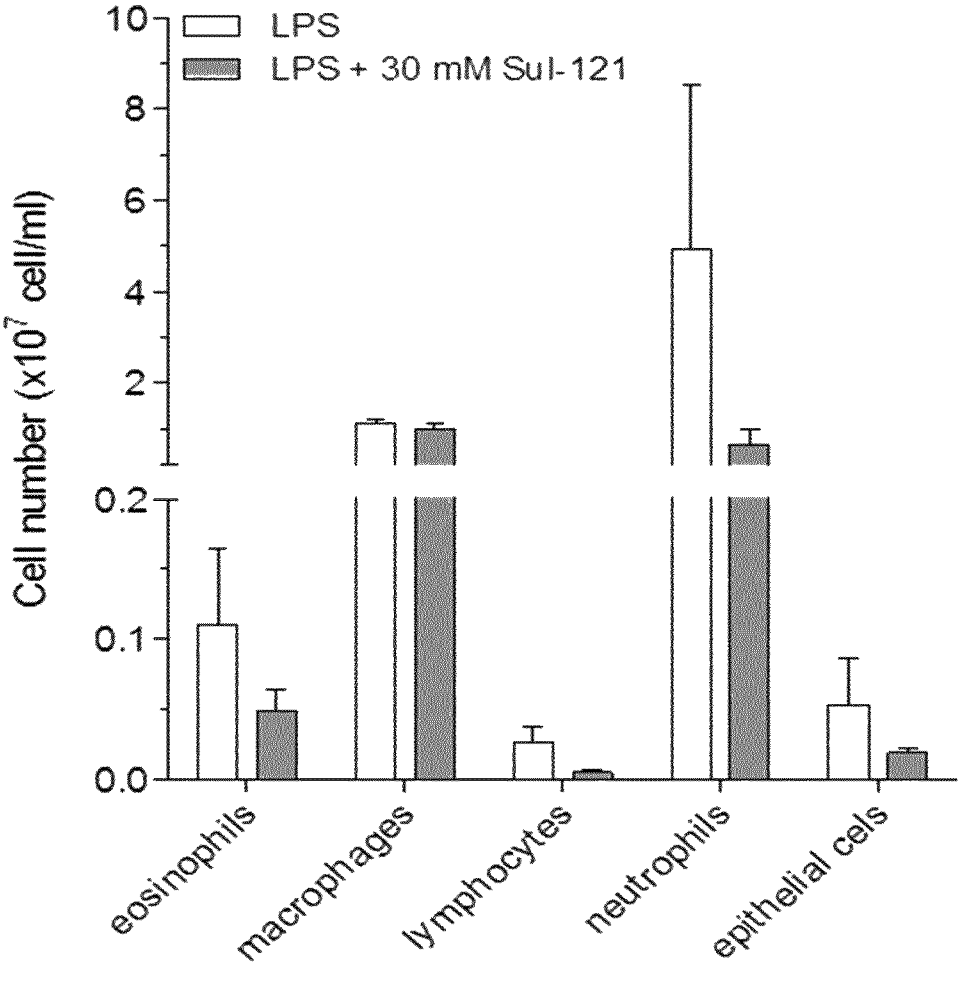
FIG. 8 shows the effect of Sul-121 on inflammatory cells in a guinea pig model after LPS challenging.

FIG. 8 shows results of the BAL measurements, and—although the error margin in the control is relatively large, the results indicate that eosinophils, lymphocytes, neutrophils and epithelial cells were all reduced. Thereby, this experiment shows that the compounds of the present invention have a reductive effect on the inflammation in vivo.

The invention claimed is:

1. A method of treating a chronic obstructive airway disease in a subject, the method comprising:

administering to the subject a compound according to the formula

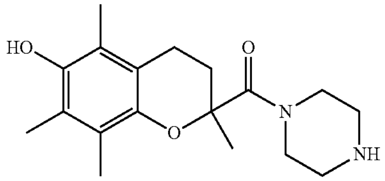

or (6-hydroxy-2,5,7,8-tetramethylchroman-2-yl)(piperazin-1-yl)methanone

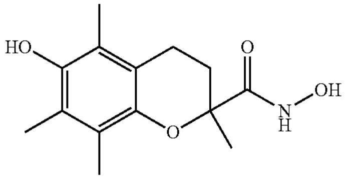

N,6-dihydroxy-2,5,7,8-tetramethylchroman-2-carboxamide or a pharmaceutically acceptable salt or base thereof to treat the subject for the chronic obstructive airway disease.

2. The method according to claim 1, wherein the administering comprises oral administration of said compound.

3. The method according to claim 2, wherein said oral administration comprises inhalation.

4. The method according to claim 1, wherein the compound is in solid form and has an aerodynamic diameter of 0.5-8 μm.

5. The method according to claim 1, wherein said chronic obstructive airway disease is chronic obstructive pulmonary disease (COPD).

6. The method according to claim 1, wherein said chronic obstructive airway disease is asthma.

7. The method according to claim 1, wherein said chronic obstructive airway disease is bronchiectasis.

8. The method according to claim 1, wherein the compound is in solid form and has an aerodynamic diameter of 1-5 μm.

* * * * *